(12) United States Patent
Takada

(10) Patent No.: US 8,506,980 B2
(45) Date of Patent: Aug. 13, 2013

(54) PERCUTANEOUSLY ABSORBABLE PREPARATION, PERCUTANEOUSLY ABSORBABLE PREPARATION HOLDING SHEET, AND PERCUTANEOUSLY ABSORBABLE PREPARATION HOLDING EQUIPMENT

(75) Inventor: Kanji Takada, Kyoto (JP)

(73) Assignee: Bioserentach Co., Ltd., Kyoto (JP)

( * ) Notice: Subject to any disclaimer, the term of this patent is extended or adjusted under 35 U.S.C. 154(b) by 166 days.

(21) Appl. No.: 12/914,456

(22) Filed: Oct. 28, 2010

(65) Prior Publication Data

US 2011/0046575 A1    Feb. 24, 2011

Related U.S. Application Data

(62) Division of application No. 11/883,118, filed as application No. PCT/JP2006/301480 on Jan. 30, 2006, now abandoned.

(30) Foreign Application Priority Data

Jan. 31, 2005  (JP) .................................. 2005-23276
Oct. 11, 2005  (JP) ................................. 2005-296691

(51) Int. Cl.
    *A61F 13/00*      (2006.01)
    *A61M 5/00*       (2006.01)

(52) U.S. Cl.
    USPC ........................................ 424/422; 604/173

(58) Field of Classification Search
    USPC ........................................ 424/422; 604/173
    See application file for complete search history.

(56) References Cited

U.S. PATENT DOCUMENTS

| | | | |
|---|---|---|---|
| 4,754,745 A * | 7/1988 | Horowitz ........................ | 600/8 |
| 5,660,846 A | 8/1997 | Cheikh | |
| 6,334,856 B1 | 1/2002 | Allen et al. | |
| 6,514,193 B2 * | 2/2003 | Kaplan ............................. | 600/7 |
| 6,638,246 B1 | 10/2003 | Naimark et al. | |
| 2001/0053891 A1 | 12/2001 | Ackley | |
| 2002/0193754 A1 | 12/2002 | Cho | |
| 2003/0135201 A1 | 7/2003 | Gonnelli | |
| 2004/0106904 A1 | 6/2004 | Gonnelli et al. | |
| 2004/0109823 A1 * | 6/2004 | Kaplan ....................... | 424/1.11 |
| 2005/0261632 A1 | 11/2005 | Xu | |

FOREIGN PATENT DOCUMENTS

| | | |
|---|---|---|
| JP | 2003-238347 | 8/2003 |
| WO | 96/07397 | 3/1996 |
| WO | 2004/000389 | 12/2003 |

OTHER PUBLICATIONS

F. Chabri et al., "Microfabricated Silicon Microneedles for Nonviral Cutaneous Gene Delivery", British Journal of Dermatology, vol. 150, pp. 869-877, 2004.
M. R. Prausnitz et al., "Microneedles for Transdermal Drug Delivery", Advanced Drug Delivery Reviews, vol. 56, pp. 581-587, 2004.
J. A. Matriano et al., "Macroflux® Microprojection Array Patch Technology: A New and Efficient Approach for Intracutaneous Immunization", Pharmaceutical Research, vol. 19, No. 1, pp. 63-70, Jan. 2002.
W. Lin et al., "Transdermal Delivery of Antisense Oligonucleotides with Microprojection Patch (Macroflux®) Technology", Pharmaceutical Research, vol. 18, No. 12, pp. 1789-1793, Dec. 2001.
D. K. Armani et al., "Microfabrication Technology for Polycaprolactone, A Biodegradable Polymer", J. Micromech. Microeng., vol. 10, pp. 80-84, 2000.
S. Henry et al., "Microfabricated Microneedles: A Novel Approach to Transdermal Drug Delivery", Journal of Pharmaceutical Sciences, vol. 87, No. 8, pp. 922-925, Aug. 1998.

* cited by examiner

*Primary Examiner* — Abigail Fisher
(74) *Attorney, Agent, or Firm* — Wenderoth, Lind & Ponack, L.L.P.

(57) ABSTRACT

Self-dissolving needle-like or filamentous shape percutaneously absorbable preparations, by which inherently poorly absorbable drugs into the body through the skin is efficiently administered. The preparations are made of at least one material selected from the group consisting of proteins, polysaccharides, polyvinyl alcohols, carboxyvinyl polymers and sodium polyacrylic acids. An active substance contained therein is released in a sustained-release fashion (1) by forming a water-insoluble layer on its surface, (2) by holding the active substance in porous materials, or (3) by imparting a long-acting characteristic to the active substance. The present invention also provides a sheet-like carrier for holding the preparations on at least one of the sides thereof, and a piece of equipment for holding the preparations so as to facilitate the administration of them.

3 Claims, 14 Drawing Sheets

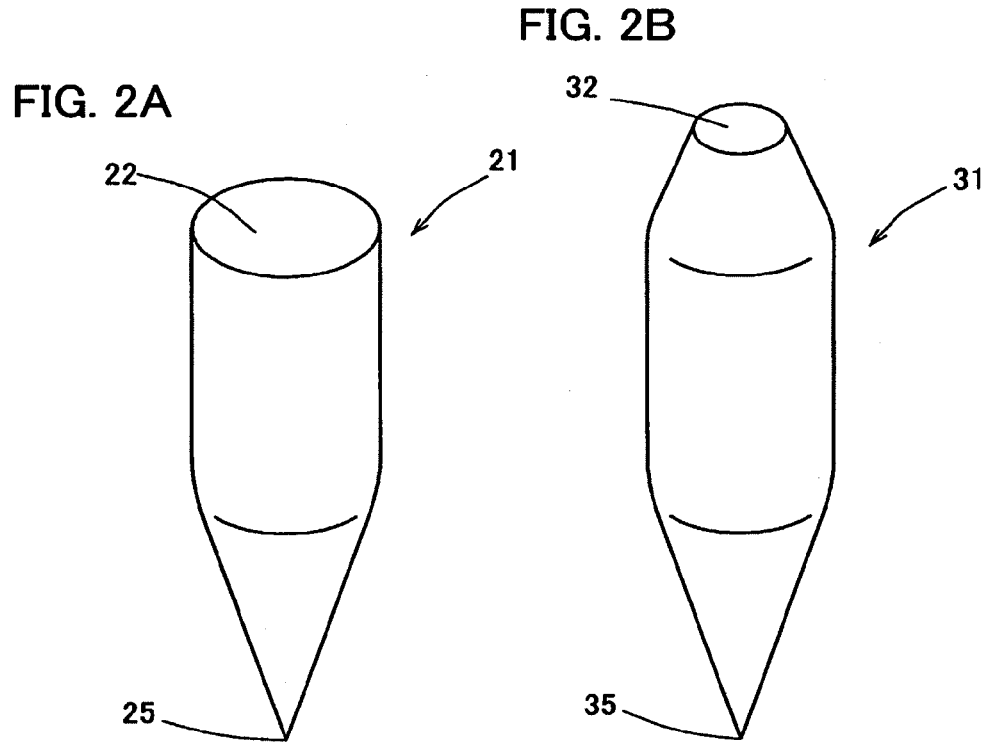
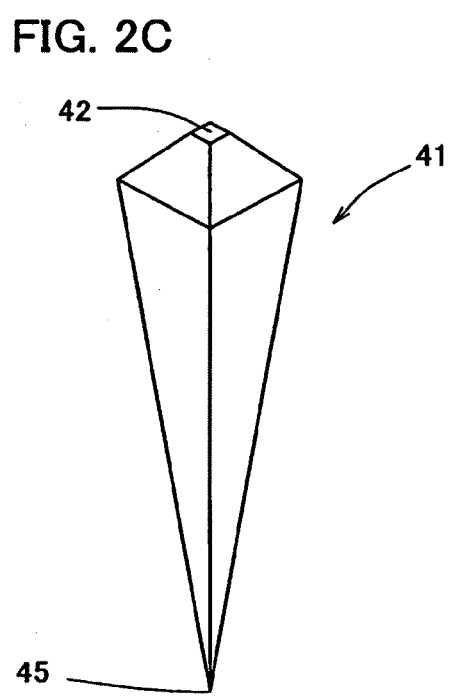

PERCUTANEOUSLY ABSORBABLE PREPARATION, PERCUTANEOUSLY ABSORBABLE PREPARATION HOLDING SHEET, AND PERCUTANEOUSLY ABSORBABLE PREPARATION HOLDING EQUIPMENT

This is a divisional of Ser. No. 11/883,118, filed Jul. 26, 2007 now abandoned, which is a U.S. national stage of International Application No. PCT/JP2006/301480 filed Jan. 30, 2006.

TECHNICAL FIELD

The present invention relates to percutaneously absorbable preparations per se, a sheet-like carrier for holding the preparations, and a piece of equipment for holding the preparations. More particularly, it relates to (1) a self-dissolving percutaneously absorbable preparation having a slender, pointed shape adapted for insertion into the skin, this shape being hereinafter referred to as "needle-like or filamentous shape", the preparations which include a base holding an active substance of proteins and polysaccharides etc., (2) a sheet-like carrier for holding the percutaneously absorbable preparations on at least one of the sides thereof, and (3) a piece, of equipment for holding the preparations in a penetration hole formed in its main body. In this specification, the term "preparations" in plural means not only a product but also products, so as to distinguish from "preparation" in singular meaning the act of preparing.

BACKGROUND ART

As one of the noninvasive methods for the administration of drugs, a drug is administered with the use of percutaneously absorbable preparations. For instance, percutaneously absorbable preparations such as ointment, cream, lotion, poultice and patch have been used. The use of these percutaneous preparations is usually limited to the local therapy of disease localized on the skin. Because of the barrier function possessed by the skin, the systemic therapy with drugs through the percutaneous route is difficult due to the low systemic availability of locally applied drugs to the skin. Though several patch type Transdermal Therapeutic Systems (TTS) have been launched onto the market, the drugs are limited to estrogen, nitric acid derivatives, tulobuterol and nicotine etc. that show their pharmacological activities at low plasma or serum concentration, i.e., their therapeutic concentrations are lower than 20 ng/mL. So far, the absorption of macromolecular drugs such as insulin through percutaneous route is difficult because of their low skin permeability and no percutaneous preparations have been developed up to now. Therefore, macromolecular drugs are still administered to patients by injections.

Under such a background, development of injection technology with low invasion has been challenged and microneedle was developed as one of those technologies. Microneedle is a fine needle having no pain when applied onto the skin. As microneedle material, not only steel as a conventional injection needle but also silicon etc, are used (Non-patent documents 1 and 2). These microneedles have holes in themselves as conventional injection needles and drug solutions are injected through these holes. In addition, self-dissolving microneedle made of base material dissolving in the body was also developed. Active substance is contained in the base and is released from microneedle by the dissolution of the base after inserted into the skin. For instance, a self-dissolving microneedle made of maltose as the base is disclosed (Patent document 1). In addition, the self-dissolving microneedles made of polylactic acid, polyglycolic acid or poly-ε-caprolactone are also known.

In addition, when the active substance is a drug that receives high clearance from the systemic circulation such as insulin, long-term pharmacological activity is needed. In such a case, self-dissolving microneedle having the function of sustained-release characteristics of the active substance is required. For instance, a self-dissolving microneedle consisting of polylactic acid has a sustained-release function of the active substance.

Patent document 1: JP2003-238347 A
Non-patent document 1: D. K. Armini and C. Lui, "Microfabrication technology for polycaprolactone, a biodegradable polymer", Journal of Micromechanics and Microengineering, 2000, 10, 80-84
Non-patent document 2: M. R. Prausnitz, "Microneedles for transdermal drug delivery", Advanced Drug Delivery Reviews, 2004, 56, 581-587

DISCLOSURE OF THE INVENTION

Problems to be Solved by the Invention

When a self-dissolving microneedle which has a base consisting of maltose is prepared, an active substance is added to the melt maltose heated to more than the melting point of maltose and thereafter the mixture is molded. Here, the melting point of maltose is high, about 102-103° C. In a microneedle which has a base consisting of maltose, an active substance to be held in the base is therefore exposed to a high temperature during its manufacturing process. However, there are many active substances that receive degradation, denaturation or inactivation at a high temperature. A self-dissolving microneedle of which base is maltose is therefore difficult to contain these active substances. Especially, when the active substances are peptides and proteins which can escape neither denaturation nor inactivation by heating, it is extremely difficult to use maltose as a base. When an active substance is insulin, denaturation and inactivation by high temperature is prevented in some degree by using insulin powder. However, since molded maltose in which powder is dispersed is fragile, a microneedle containing maltose as a base and insulin powder held therein is difficult to keep its physical strength. Further, since maltose has a strong hygroscopicity, a self-dissolving microneedle which has a base consisting of maltose adsorbs moisture as the time passes and the top of the microneedle becomes soft. As a result, it has a pitfall, i.e. unavailability for the insertion into the skin. Therefore, it may be difficult for a self-dissolving microneedle containing maltose as a base to administer an active substance quantitatively.

Still further, when polylactic acid, a water-insoluble polymer, is used as a base for a microneedle to obtain sustained-release characteristics of the active substance, polylactic acid needs to be dissolved with an organic solvent such as methylene chloride. However, some active substances receive denaturation or inactivation by exposure to organic solvents. For instance, when proteins or peptides such as insulin are employed as an active substance, they are easily denatured or inactivated by exposure to an organic solvent. Therefore, a self-dissolving microneedle which has a base consisting of a water-soluble material and has sustained-release characteristics is desired.

The primary object of the present invention is to provide a needle-like or filamentous shape self-dissolving percutaneously absorbable preparation, hereinafter being sometimes referred to merely as "preparations", having suitable physical strength for the percutaneous delivery of poorly absorbable drugs through a percutaneous route by producing at relatively low temperature without the use of any organic solvent.

Means to Solve the Problems

To solve the above mentioned problems, the inventor has succeeded to invent needle-like or filamentous shape self-dissolving percutaneously absorbable preparations that are prepared in room or under low temperature conditions through many studies concerning the screening of the base materials. The inventor has also succeeded to invent needle-like or filamentous shape self-dissolving percutaneously absorbable preparations having sustained-release characteristics of active substance without polylactic acid. In addition, the inventor has succeeded in preparing the percutaneously absorbable preparations holding sheet-like carrier by which the percutaneously absorbable preparations are administered percutaneously with high efficiency. Furthermore, the inventor has completed this invention by preparing percutaneously absorbable preparations holding equipment by which needle-like or filamentous shape percutaneously absorbable preparations are inserted into the skin with ease. The present invention will be described hereinafter.

According to a first aspect of percutaneously absorbable preparations of the present invention, percutaneously absorbable preparations having a base of water-soluble and biologically soluble polymer material, and an active substance held in the base are characterized by having a slender, pointed shape, such as a needle-like or filamentous shape, adapted for insertion into skin to percutaneously administer the active substance into the body, wherein the polymer material is at least one material selected from the group consisting of proteins, polysaccharides, polyvinyl alcohols, carboxyvinyl polymers and sodium polyacrylic acids.

The percutaneously absorbable preparations in this aspect are a self-dissolving percutaneously absorbable type which make an objective substance to be absorbed through skin into the body by inserting the preparations into the skin, and which has a base consisting of water-soluble and biologically soluble macromolecular substances and an objective substance held in the base. In the percutaneously absorbable preparations in this aspect, the base is made of at least one material selected from the group consisting of proteins, polysaccharides, polyvinyl alcohols, carboxyvinyl polymers and sodium polyacrylic acids, and the preparations have a needle-like or a filamentous shape. The percutaneously absorbable preparations in this aspect can be manufactured at room temperature or at relatively low temperature, because the base consists of protein etc. Therefore, the objective substance is not exposed to high temperature during the manufacturing process. More specifically, even though the objective substance is inherently unstable at high temperature, it does not lose its activity during the manufacturing process. As a result, the active substance is able to be absorbed through skin in high efficiency by the use of the percutaneously absorbable preparations in this aspect.

The proteins, polysaccharides, polyvinyl alcohols, carboxyvinyl polymers and sodium polyacrylic acids that are used as a base of the percutaneously absorbable preparations in this aspect belong to "the substance having thread-forming property" that becomes gluey when dissolved in a small amount of water.

According to a second aspect of percutaneously absorbable preparations of the present invention, percutaneously absorbable preparations having a base of water-soluble and biologically soluble polymer material, and an active substance held in the base, are characterized by having a slender, pointed shape, such as a needle-like or filamentous shape, adapted for insertion into skin to percutaneously administer the active substance into the body, wherein the percutaneously absorbable preparations have a water-insoluble layer formed on the surface thereof, and wherein the active substance is released in a sustained-release fashion.

The advantage of the percutaneously absorbable preparations in this aspect is in the capability of sustained-releasing the active substance. More specifically, the percutaneously absorbable preparations have a water-soluble and biologically soluble macromolecular base and an active substance held in the base. The active substance is percutaneously administered into the body, wherein the preparation is provided with a water-insoluble layer formed on its surface. In the percutaneously absorbable preparations in this aspect, no organic solvent is used during the manufacturing process of the base, because the base consists of water-soluble materials. More specifically, since the active substance held in the base is not exposed to organic solvent, the active substance potentially keeps its activity during the manufacturing process. As a result, the active substance is percutaneously administered to the body highly efficiently by the percutaneously absorbable preparations in this aspect. In addition, the percutaneously absorbable preparations in this aspect are easily manufactured as the active substance has sustained-release characteristics by forming a water-insoluble layer on its surface.

Preferably, the water-insoluble layer is formed by cross-reaction.

The percutaneously absorbable preparations of the preferred aspect are easily manufactured.

According to a third aspect of percutaneously absorbable preparations of the present invention, percutaneously absorbable preparations having a base of water-soluble and biologically soluble polymer material, and an active substance held in the base, are characterized by having a slender, pointed shape, such as a needle-like or filamentous shape, adapted for insertion into skin to percutaneously administer the active substance into the body; wherein the base contains a porous compound, and wherein the active substance is held in the porous compound and is released in a sustained-release fashion.

Preferably, the porous material is at least one material selected from the group consisting of calcium silicate, aluminum silicate, magnesium silicate, anhydrous silicate, porous calcium carbonate, porous calcium phosphate and porous silicon.

The percutaneously absorbable preparations in this aspect are needle-like or filamentous shape self-dissolving percutaneously absorbable preparations having a sustained-release function of the active substance. More specifically, the percutaneously absorbable preparations have a water-soluble and biologically soluble macromolecular base and an active substance held in the base and the active substance is percutaneously administered into the body, wherein the active substance is held in porous materials contained in the base. In the percutaneously absorbable preparations in this aspect, no organic solvent is used during the manufacturing process of the base, because the base consists of water-soluble materials. More specifically, since the active substance held in the base is kept from exposure to organic solvent, the active substance remains active during the manufacturing process. As a result, the active substance is administered percutaneously into the body highly efficiently by the percutaneously absorbable preparations in this aspect. In addition, the percutaneously absorbable preparations in this aspect do not need a special treatment to allow the active substance to possess sustained-release characteristics, because the active substance is held in porous materials contained in the base.

According to a fourth aspect of percutaneously absorbable preparations of the present invention, percutaneously absorbable preparations having a base of water-soluble and biologically soluble polymer material, and an active substance held in the base, is characterized by having a slender, pointed shape, such as a needle-like or filamentous shape, adapted for insertion into skin to percutaneously administer the active substance into the body, wherein the active substance is a long-acting material and is released in a sustained-release fashion.

Preferably, the long-acting substance is long-acting type insulin or protein cross-linked with polyethylene glycol.

The percutaneously absorbable preparations in this aspect have sustained-release characteristics of active substances. More specifically, the percutaneously absorbable preparations have a water-soluble biologically soluble macromolecular base and an active substance held in the base, and the active substance is percutaneously administered into the body, wherein the active substance is a long-acting substance. No organic solvent is used to prepare the base in the percutaneously absorbable preparations, because the base consists of a water-soluble substance. More specifically, the active substance remains active during the manufacturing process, since the active substance held in the base is kept from exposure to the organic solvent. As a result, the active substance is highly efficiently absorbed through the skin. Furthermore, no special treatment is needed to obtain the sustained-release characteristics of the active substance, since a long-acting substance is used as the active substance. Examples of the long-acting substance include long-acting insulin and polyethylene glycol complexed proteins.

Preferably, the polymer material is at least one material selected from the group consisting of proteins, polysaccharides, polyvinyl alcohols, carboxyvinyl polymers and sodium polyacrylic acids.

The percutaneously absorbable preparations in this preferred aspect is prepared at room temperature or at relatively low temperature, because the base is made of protein etc. Therefore, the active substance held on the base is kept from exposure to high temperature during the manufacturing process. More specifically, though the active substance is inherently unstable at high temperature, it does not loss the activity during manufacturing process. As a result, the active substance is highly efficiently administered percutaneously into the body by the percutaneously absorbable preparations.

Preferably, the protein is at least one material selected from the group consisting of serum albumin, serum α-acid glycoprotein and gelatin.

Preferably, the polysaccharide is at least one material selected from the group consisting of glycogen, dextrin, dextran, dextran sulfate, sodium chondroitin sulfate, hydroxy propyl cellulose, alginic acid, agarose, chitin, chitosan, pullulan and hyaluronic acid.

The percutaneously absorbable preparations in these preferred aspects ensure hygienic safety, because the base is made of pharmaceutical preparations whose safety is generally acknowledged.

Preferably, the base contains an absorption rate controller for controlling the absorption rate of the active substance.

Preferably, the absorption rate controller is an absorption enhancer.

Preferably, the absorption enhancer is a surfactant.

In such preferred aspects, the dissolution rate and permeability of the active substance is accelerated by the action of surfactant even when the active substance has a low solubility and a low permeability in the epidermis and dermis of the skin. As a result, the active substance is effectively percutaneously administered into the body.

Preferably, the base contains a thread-reducing agent, thereby reducing the thread-forming property thereof.

Preferably, the thread-reducing agent is polyethylene glycol or L-glutamic acid L-lysine.

According to the preferred aspects, the thread-forming property of the base is reduced. Since the thread-forming property of the base is well controlled, the preparations are smoothly manufactured.

Preferably, the active substance is a drug.

The use of the drug-base percutaneously absorbable preparations ensures that the active substance is effectively administered percutaneously into the body for the therapy, prophylaxis and diagnosis of disease.

Preferably, the drug falls in peptides, proteins, nucleic acids, polysaccharides or vaccine.

According to the preferred aspect, percutaneously poorly absorbable drugs like peptides, proteins, nucleic acids, polysaccharides and vaccine are administered percutaneously into the body.

Preferably, the base contains a stabilizer for stabilizing the active substance.

In this case, the active substance held in the base is stabilized by the action of the stabilizer. As a result, a possible inactivation or any other inadequacy of the active substance is eliminated. When the active substance is peptides or proteins, a protease inhibitor and a nuclease inhibitor are desirably used for peptides/proteins and nucleic acids, respectively.

Preferably, the preparations further include a moisture-proof layer formed on the surface thereof.

Thus, the percutaneously absorbable preparation can have a reduced hygroscopicity because of the existence of the moisture-proof layer on its surface. As a result, the top of the preparations is prevented from softening, and the percutaneously absorbable preparations are inserted into the skin. The active substance is administered exactly to a desired quantity.

Preferably, the preparations are constricted or have a secant in part on the surface thereof.

The percutaneously absorbable preparations in this preferred aspect are constricted or have a secant on the part or parts of their surface, and are cut along the constricted portion or the secant after the preparations are inserted into the skin. As a result, the part or parts of the preparations, from the secant to the top, are inserted into the skin and the active substance is accurately dosed.

According to a fifth aspect of percutaneously absorbable preparations of the present invention, the percutaneously absorbable preparations are characterized in at least two of the preparations of any one of the above-described aspects linked in series.

According to this aspect, the linked series of preparations are sequentially administered into the body through the skin.

According to an aspect of a sheet-like carrier of the present invention, there is provided a sheet-like carrier for holding at least one of the percutaneously absorbable preparations on at least one of the surfaces thereof, wherein the preparations held on the carrier are inserted into the skin by pushing the carrier thereonto.

The present aspect is directed to a sheet-like carrier for holding the percutaneously absorbable preparations, wherein at least one of the percutaneously absorbable preparations except the fifth aspect are held on the sheet-like carrier and the percutaneously absorbable preparations are inserted into the skin by pressing the sheet-like carrier onto the skin. As a result, the percutaneously absorbable preparations held on the sheet-like carrier are inserted into the skin. According to this aspect, the percutaneously absorbable preparations are highly efficiently administered.

According to an aspect of equipment of the present invention, there is provided a piece of equipment for holding percutaneously absorbable preparations including having a base of water-soluble and biologically soluble polymer material, an active substance held in the base, and having a slender, pointed shape, such as a needle-like or filamentous shape, adapted for insertion into skin to percutaneously administer the active substance into the body, the equipment including a main body having a penetration hole in and along which the preparations are moved.

According to another aspect of equipment of the present invention, there is provided a piece of equipment for holding percutaneously absorbable preparations, the equipment including a main body having a penetration hole in and along which the preparations are moved, wherein the preparations fall in any one of the above-described aspects.

In the equipment in these aspects, the percutaneously absorbable preparations move in and along the penetration hole, and are inserted into the skin by pushing out the preparations from the other end of the penetration hole. As a result, the preparations are accurately and easily inserted into the skin.

Preferably, the penetration hole accommodates a spacer kept in contact with the preparations held in the penetration hole, so that the spacer moves in and along the penetration hole while being kept in contact with the preparations.

When the preparations held in the penetration hole are pushed to the skin, a pushing unit is inserted into the hole to push it out from the other end of the hole. At the time when the percutaneously absorbable preparations are completely inserted into the skin, the pushing unit comes into contact with the skin. However, a small amount of the body fluid may leak on the skin at a spot where the preparations are inserted, and the body fluid may adhere to the pushing unit. More specifically, when several pieces of equipment are used one after another as if they are cartridges, the patients are in danger of being infected through the body fluid. The equipment in the preferred aspect has a spacer, which is kept in contact with the percutaneously absorbable preparations in the penetration hole. The spacer moves in and along the penetration hole. By use of this equipment, the percutaneously absorbable preparations are pushed via the spacer by a pushing unit. As a result, the pushing unit does not come into contact with the skin at the point when the preparations are completely inserted into the skin. Therefore, by use of the equipment, there is no fear of infection through the body fluid among the patients even if a plurality of equipment are used one after another as if they are cartridges.

Preferably, the main body includes a concave to which the penetration hole is open.

Owing to the presence of the concave, the preparations are easily released under the pushing urge. In addition, the concave makes it easy to attach the pushing unit to the equipment.

Preferably, the concave includes female threads cut on the inside wall thereof.

The equipment has female threads formed at its concave. Therefore, the pushing unit having male threads is certainly attached to the equipment.

Preferably, the main body is made of plastics.

The equipment is lightweight, and is convenient for use. In addition, there is no fear of metallic allergy because it is not made of metal.

Advantageous Effect of the Invention

By use of the percutaneously absorbable preparations embodying the present invention, even if the active substance is a percutaneously poorly absorbable drug, it is efficiently administered percutaneously into the body.

By use of the sheet-like carrier embodying the present invention, the percutaneously absorbable preparations are highly efficiently administered.

By use of the equipment embodying the invention, the needle-like or filamentous shape percutaneously absorbable preparations are easily administered with high accuracy.

BRIEF DESCRIPTION OF THE DRAWINGS

FIG. 2A is a perspective view showing a modified version of the percutaneously absorbable preparations of FIG. 1A; FIG. 2B is a perspective view showing another modified version of the percutaneously absorbable preparations of FIG. 1A; and FIG. 2C is a perspective view showing a modified version of the percutaneously absorbable preparations of FIG. 1B.

DESCRIPTION OF THE NUMERALS

| 1, 1a-1q: | percutaneously absorbable preparation |
|---|---|
| 21: | percutaneously absorbable preparation |
| 31: | percutaneously absorbable preparation |
| 41, 41a-41d: | percutaneously absorbable preparation |
| 51: | percutaneously absorbable preparation |
| 61: | percutaneously absorbable preparation |
| 66: | secant |
| 67: | constricted line |
| 71: | percutaneously absorbable preparation |
| 76a, 76b: | secant |
| 81: | percutaneously absorbable preparation |
| 91: | base |
| 100: | sheet-like carrier for holding the percutaneously absorbable preparation |
| 102: | supporting body |
| 110: | percutaneously absorbable preparations holding equipment |
| 111: | percutaneously absorbable preparation |
| 112: | main body |
| 113: | penetration hole |
| 115: | bead (spacer) |
| 117: | concave |
| 120: | percutaneously absorbable preparations holding equipment |
| 121: | percutaneously absorbable preparation |
| 130: | percutaneously absorbable preparations holding equipment |
| 131: | percutaneously absorbable preparation |
| 140: | percutaneously absorbable preparations holding equipment |
| 147: | concave |

DESCRIPTION OF THE PREFERRED EMBODIMENTS

Hereinafter, preferred embodiments of the present invention will be described in detail.

Figure 1A:
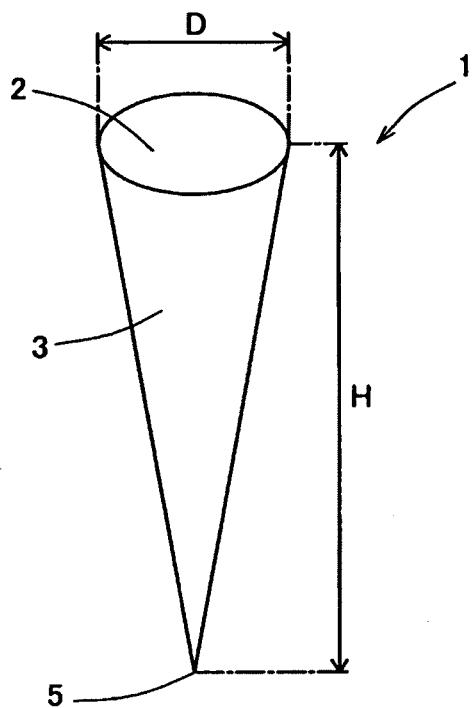
FIG. 1A is a perspective view showing an embodiment of the needle-like percutaneously absorbable preparations.
Figure 1B:
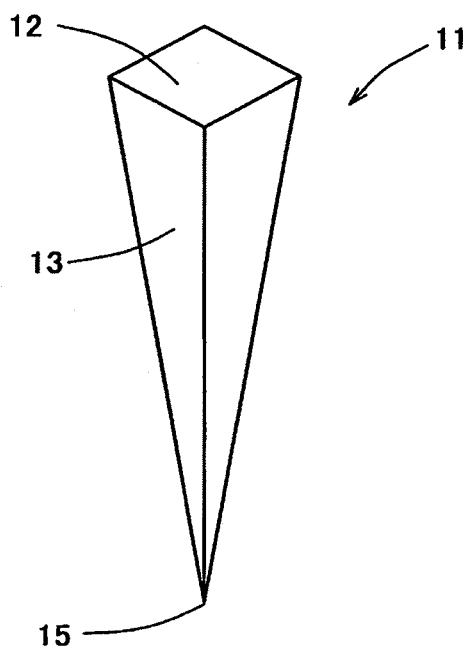
FIG. 1B is a perspective view which shows another embodiment of the needle-like percutaneously absorbable preparations.
Figure 3:
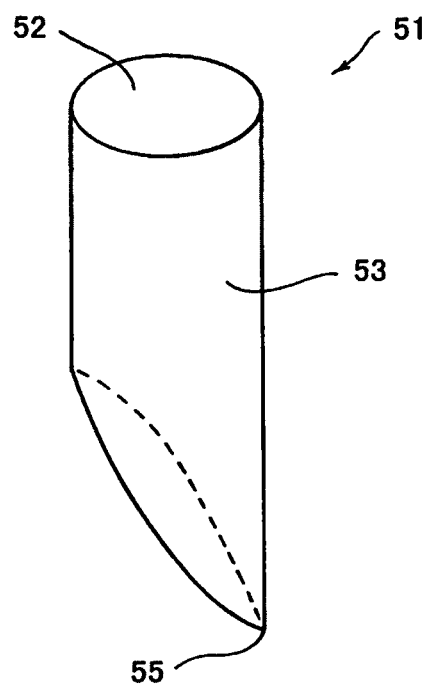
FIG. 3 is a perspective view showing an embodiment of the filamentous percutaneously absorbable preparations.

All the percutaneously absorbable preparations of the present invention have a generally slender, pointed shape; herein, this shape being referred to as "needle-like or filamentous shape". Examples of "needle-like" and "filamentous" percutaneously absorbable preparations according to the present invention are illustrated by the accompanying drawings; FIGS. 1A and 1B show examples of percutaneously absorbable preparations having a needle-like or filamentous shape. FIG. 1A is a perspective view showing an embodiment of the needle-like percutaneously absorbable preparations. FIG. 1B is a perspective view which shows another embodiment of the needle-like percutaneously absorbable preparations. FIGS. 2A, 2B and 2C show modified versions of percutaneously absorbable preparations of FIGS. 1A and 1B. FIG. 2A is a perspective view showing a modified version of the percutaneously absorbable preparations of FIG. 1A. FIG. 2B is a perspective view showing another modified version of the percutaneously absorbable preparations of FIG. 1A. FIG. 2C is a perspective view showing a modified version of the percutaneously absorbable preparations of FIG. 1B. FIG. 3 is a perspective view showing an embodiment of the filamentous percutaneously absorbable preparations.

Percutaneously absorbable preparation 1 shown in FIG. 1A has a substantially conical shape, and has a substantially circular pushing part 2, a surface 3 consisting of a curved surface, and a pointed top 5. Percutaneously absorbable preparation 1 is inserted into the skin by pushing the pushing part 2 under the condition that the top 5 is kept in contact with the skin. The diameter D of the pushing part 2 is in a range of about 0.1-500 μm. The length H of the percutaneously absorbable preparation 1 is in a range of about 0.5-1500 μm. The numerical values of 500 μm which is the maximum value of the diameter D and 1500 μm which is the maximum value of the length are bigger than the diameter and length of the usual microneedles. More specifically, percutaneously absorbable preparation 1 includes not only conventional microneedles but also larger size microneedles. On the other hand, percutaneously absorbable preparation 11 shown in FIG. 1B has a substantially quadrilateral shape, and has a substantially square pushing part 12, a surface 13 consisting of four planes, and a pointed top 15. It is inserted into the skin by pushing the pushing part 12 under the condition that the top 15 is in contact to the skin. Percutaneously absorbable preparation 11 has the same size as percutaneously absorbable preparation 1 shown in FIG. 1A. In the percutaneously absorbable preparation 11 shown in FIG. 1B, though the pushing part 12 is substantially square, another polygonal shape is accepted.

Percutaneously absorbable preparation 21 shown in FIG. 2A is a modified version of the percutaneously absorbable preparation 1 shown in FIG. 1A, and has a shape of a nail whose top is sharpened. As the percutaneously absorbable preparation 1, percutaneously absorbable preparation 21 is inserted into the skin by pushing a pushing part 22 under the condition that a top 25 is in contact with the skin. Percutaneously absorbable preparation 31 shown in FIG. 2B is another modified version of the percutaneously absorbable preparation 1 and has a shape of the percutaneously absorbable preparation 21 shown in FIG. 2A with a truncated cone placed on the pushing part 2. Percutaneously absorbable preparation 31 is also inserted into the skin by pushing a pushing part 32 under the condition that a top 35 is kept in contact with the skin. Percutaneously absorbable preparation 41 shown in FIG. 2C has a shape of the percutaneously absorbable preparation 21 shown in FIG. 1B with a square pyramid placed on the pushing part 2. Percutaneously absorbable preparation 41 is also inserted into the skin by pushing a pushing part 42 under the condition that a top 45 is in contact with the skin. As mentioned above, percutaneously absorbable preparations shown in FIGS. 1A-1B and 2A-2C are all needle-like.

On the other hand, percutaneously absorbable preparation 51 shown in FIG. 3 is a filamentous solid preparation that has a shape as if a circular cylinder is diagonally cut. Percutaneously absorbable preparation 51 has a pushing part 52 having a substantially circular shape, a surface 53 consisting of a curved surface, and a pointed top 55. Percutaneously absorbable preparation 51 is inserted into the skin by pushing the pushing part 52 under the condition that the top 55 is in contact with the skin. The percutaneously absorbable preparation 51 has the same size as the percutaneously absorbable preparation 1 shown in FIG. 1A or the percutaneously absorbable preparation 11 as shown in FIG. 1B. The expression "Filamentous" is replaced with the expression "Cylinder shape".

All the percutaneously absorbable preparations of the present invention are those having a base of water-soluble and biologically soluble polymer material, and an active substance held in the base, including, having a slender, pointed shape, such as a needle-like or filamentous shape, adapted for insertion into skin to percutaneously administer the active substance into the body. Percutaneously absorbable preparations of the present invention are chiefly composed of five aspects. A first aspect relates to a conventional preparation. Second, third and fourth aspects relate to a sustained-release preparation. A fifth aspect relates to a percutaneously absorbable preparation having at least two percutaneously absorbable preparations linked in series.

In the first aspect of the percutaneously absorbable preparations of this invention, the base consists of at least one material selected from the group consisting of proteins, polysaccharides, polyvinyl alcohols, carboxyvinyl polymers and sodium polyacrylic acids. These polymer materials each allow a stand-alone use or alternatively, a combination use with one or more other kinds. The method to hold the active substance in the base is not limited particularly, and various methods are applied. For instance, the active substance is held by the base by maintaining the active substance in the base as supramolecules. As other examples, the active substance is held in the base by adding the active substance to the dissolved base as suspension and thereafter solidified.

In the second aspect of the percutaneously absorbable preparations of this invention, a water-insoluble layer is formed on the surface, and the active substance is released in a sustained-release fashion. In a preferred embodiment of this aspect, the water-insoluble layer is formed by a cross-linking reaction. As the method to make a cross-linking reaction on the surface, for example, cross-linking reaction by treating the surface with glutaraldehyde is proposed. Precisely, percutaneously absorbable preparations are soaked in glutaraldehyde solution. As another method to make a water-insoluble layer on the surface except a cross-linking reaction, the SiO thin film formation reaction by the gas phase reaction used in the semiconductor field is applied. As another example, the method to make the surface insoluble by keeping under the condition of the high temperature and high humidity is applicable when gelatin etc. is used as the base, though this method is used in the field of capsule technology. Still another method is to soak the percutaneously absorbable preparations in a saturated calcium chloride solution. On the other hand, as the method to hold active substance in the base, for example, the same method as described in the first aspect of the percutaneously absorbable preparations is applied.

In the third aspect of the percutaneously absorbable preparations of this invention, the base contains a porous compound. The active substance is held in the porous compound, and is released in a sustained-release fashion. In a preferred embodiment of this aspect, the porous material is at least one material selected from the group consisting of calcium silicate, aluminum silicate, magnesium silicate, anhydrous silicate, porous calcium carbonate, porous calcium phosphate and porous silicon. These porous materials each allow a stand-alone use or alternatively, a combination use with one or more other kinds. These porous materials are commercially obtainable, and may be used without modification. For instance, calcium silicate includes Florite (Trade name, Eisai Co., Ltd., Tokyo, Japan). Aluminum silicate and magnesium silicate includes Neusilin (Registered trademark, Fuji Chemical Industry Co., Ltd., Toyama, Japan). Silicon dioxide includes Sylysia (Trade name, Fuji Silysia Co., Ltd., Aichi, Japan). Porous silicone includes BioSilicon (Trade name, pSivida Inc.). In addition, porous calcium carbonate and porous calcium phosphate are obtainable from National Institute for Materials, Japan, for instance.

In the fourth aspect of the percutaneously absorbable preparations of this invention, the active substance is a long-acting material and is released in a sustained-release fashion. In a preferred embodiment of this aspect, the long-acting substance is long-acting type insulin or protein cross-linked with polyethylene glycol. Specific examples of the long-acting insulin include middle-acting, long-acting and ultra-long-acting insulins. Specific examples of the polyethylene glycol cross-linked protein include PEG-modified proteins such as PEG-interferon and PEG-erythropoietin.

In a preferred embodiment which is common to percutaneously absorbable preparations of the above-mentioned second, third, and fourth aspects, the base consists of at least one material selected from the group consisting of proteins, polysaccharides, polyvinyl alcohols, carboxyvinyl polymers and sodium polyacrylic acids, as with the first aspect. These macromolecules each allow a stand-alone use or alternatively, a combination use with one or more other kinds.

Preferred embodiments common to percutaneously absorbable preparations of the above-mentioned four aspects are described below. In a preferred embodiment, the protein is at least one material selected from the group consisting of serum albumin, serum α-acid glycoprotein and gelatin. These proteins each allow a stand-alone use or alternatively, a combination use with one or more other kinds. Further, in a preferred embodiment, the polysaccharide is at least one material selected from the group consisting of glycogen, dextrin, dextran, dextran sulfate, sodium chondroitin sulfate, hydroxy propyl cellulose, alginic acid, agarose, chitin, chitosan, pullulan, and hyaluronic acid. These polysaccharides each allow a stand-alone use or alternatively, a combination use with one or more other kinds. With respect to the molecular weight of the polysaccharides, for example, hyaluronic acid with a molecular weight of up to about 1,200,000 can be used, though low molecular weight hyaluronic acid of about 90,000 is particularly preferable. For dextran, for instance, dextran of which molecular weight is not less than 50,000 can be used. For dextran sulfate, dextran sulfate of which molecular weight is about 500,000 can be used. For hydroxypropyl cellulose, low-substituted hydroxypropyl cellulose is preferably used.

In a preferred embodiment, the base contains an absorption rate controller for controlling the absorption rate of the active substance. In a further preferred embodiment, the absorption rate controller is an absorption enhancer. In a still further preferred embodiment, the absorption enhancer is a surfactant. Examples of the absorption enhancer include fatty acids such as caprylic acid, capric acid and its derivatives, N-8-(2-hydroxybenzoyl) amino caprylic acid (SNAC), and sodium N-8-(2-hydroxybenzoyl) amino decanate (SNAD); glycyrrhizin; glycyrrhizinic acid; amino acid enamine derivatives such as ethyl acetoacetate ethylenamine derivatives of phenylglycine; sodium salicylate and its derivatives; mixed micelles such as mixed micelles of mono-olein and sodium glycocholate, and mixed micelles of mono-olein and sodium taurocholates; N-acylcollagen peptide; sodium acylamino acid; *Plectranthus japonicus* saponin; bile acids; chelate compounds such as EDTA; organic acids such as citric acids and tartaric acids. However, the absorption enhancer used in this embodiment is not limited particularly to these materials.

Surfactant as an absorption enhancer is used to increase the bioavailability and pharmacological activity of the active substance by accelerating the dissolution rate of the active substance with low solubility in the surface and the dermis of the skin and by enhancing the absorption of the active substance having low membrane permeability through the skin. Examples of the surfactant include glycerin fatty acid esters, commercially available as "Ryoto (registered trademark) Polyglyester" supplied by Mitsubishikagaku Foods Co. Ltd., such as decaglycerine lauric acid esters L-7D and L-10D; decaglycerine myristic acid ester M-10D; decaglycerine stearic acid esters SWA-10D, SWA-15D, SWA-20D, S-24D and S-28D; decaglycerine oleic acid esters O-15D and O-50D; decaglycerine behenic acid esters B-70D and B-100D; decaglycerine erucic acid esters ER-30D and ER-60D; decaglecerine mixed fatty acid ester LOP-120DP; polyglycerine stearic acid esters DS13W, DS3, HS11, HS9, TS4 and TS2; polyglycerine lauric acid ester DL15; and polyglycerine oleic acid ester DO13.

Further, examples of the surfactant include stearoyl calcium lactate, sorbitan fatty acid ester, and propylene glycol fatty acid ester. Further, the examples include fatty acid sugar esters, commercially available as "Ryoto (registered trademark) Sugarester" supplied by Mitsubishikagaku Foods Co. Ltd., such as S-1670, S-1570, S-1170, P-1570, P-1670, M-1695, O-1570, OWA 1570, and L-1695. Further, the examples include DK esters F-160, F-140, and F-110 (Daiichi Kogyo Seiyaku Co., Ltd.). Further, the examples include polysorbate 80, monooleic acid, polyethylene glycol monooleate, polyethylene glycol monostearate, and middle chain fatty acid triglycerides. Further, the examples include the saturated fatty acids (C.sub 6 to C.sub 12) such as caproic acid, caprylic acid, capric acid, lauric acid, and lecithin.

Still further, liquid, semi-solid or solid surfactants except the above mentioned surfactants are used in this embodiment. These surfactants are described separately with three categories, namely, non-ionic surfactants, hydrophilic surfactants and ionic surfactants.

(a) Nonionic Surfactant
alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols; polyoxyethylene vegetable oils; polyoxyethylene hydrogenated vegetable oils; reaction mixtures of polyols with at least one selected from the group consisting of fatty acids, glycerides, vegetable oils, hydrogenated vegetable oils, and sterols; sugar esters, sugar ethers; sucroglycerides; and mixtures thereof.

(b) Hydrophilic Surfactants
PEG-10 laurate; PEG-12 laurate; PEG-20 laurate; PEG-32 laurate; PEG-32 dilaurate; PEG-12 oleate; PEG-15 oleate; PEG-20 oleate; PEG-20 dioleate; PEG-32 oleate; PEG-200 oleate; PEG-400 oleate; PEG-15 stearate; PEG-32 distearate; PEG-40 stearate; PEG-100 stearate; PEG-20 dilaurate; PEG-25 glyceryl trioleate; PEG-32 dioleate; PEG-20 glyceryl laurate; PEG-30 glyceryl laurate; PEG-20 glyceryl stearate; PEG-20 glyceryl oleate; PEG-30 glyceryl oleate; PEG-30 glyceryl laurate; PEG-40 glyceryl laurate; PEG-40 palm kernel oil; PEG-50 hydrogenated castor oil; PEG-40 castor oil; PEG-35 castor oil; PEG-60 castor oil; PEG-40 hydrogenated castor oil; PEG-60 hydrogenated castor oil; PEG-60 corn oil; PEG-6 caprate/caprylate glycerides; PEG-8 caprate/caprylate glycerides; polyglyceryl-10 laurate; PEG-30 cholesterol; PEG-25 phyto sterol; PEG-30 soya sterol; PEG-20 trioleate; PEG-40 sorbitan oleate; PEG-80 sorbitan laurate; polysorbate 20; polysorbate 80; POE-9 lauryl ether; POE-23 lauryl ether; POE-10 oleyl ether; POE-20 oleyl ether; POE-20 stearyl ether; tocopheryl PEG-100 succinate; PEG-24 cholesterol; polyglyceryl-10 oleate; Tween 40; Tween 60; sucrose monostearate; sucrose monolaurate; sucrose monopalmitate; PEG 10-100 nonyl phenol series; PEG 15-100 octyl phenol series; and poloxamer; and mixtures thereof.

(c) Ionic Surfactants
alkyl ammonium salts; bile acids and salts; fusidic acid; fatty acid conjugates of amino acids, oligopeptides, or polypeptides; glyceride esters of polypeptides; acyl lactylates; mono- and diacetylated tartaric acid esters of mono- and diglycerides; succinylated monoglycerides; citric acid esters of mono- and diglycerides; alginate salts; propylene glycol alginate; lecithins; hydrogenated lecithins; lysolecithin; hydrogenated lysolecithins; lysophospholipids; phospholipids; salts of alkylsulfates; and salts of fatty acids.

Typical examples of the ionic surfactants include the following: phosphatidylcholine; phosphatidylethanolamine; phosphatidylglycerol; phosphatidic acid; phosphatidylserine; lysophosphatidylcholine; lysophosphatidylethanolamine; lysophosphatidylglycerol; lysophosphatidic acid; lysophosphatidylserine; PEG-phosphatidylethanolamine; PVP-phosphatidylethanolamine; lactylic esters of fatty acids; stearoyl-2-lactylate; succinylated monoglycerides; mono/diacetylated tartaric acid esters of mono/diglycerides; citric acid esters of mono/diglycerides; cholate; taurocholate; glycocholate; deoxycholate; taurodeoxycholate; chenodeoxycholate; glycodeoxycholate; glycochenodeoxycholate; taurochenodeoxycholate; ursodeoxycholate; lithocholate; tauroursodeoxycholate; glycoursodeoxycholate; cholylsarcosine; N-methyl taurocholate; caproate; caprylate; caprate; laurate; myristate; palmitate; oleate; ricinoleate; linoleate; linolenate; stearate; lauryl sulfate; teracecyl sulfate; docusate; lauroyl carnitines; palmitoyl carnitines; myristoyl carnitines; and salts thereof; and mixtures of them including salts.

These surfactants also have a function of plasticizer. For instance, both absorption enhancing effect and stabilizing effect on the physical strength of percutaneously absorbable preparations are obtained by formulating polysorbate 80 into the base consisting of serum albumin.

In a preferred embodiment, the base contains a thread-reducing agent, thereby reducing the thread-forming property thereof. It has an advantage in manufacturing, because the thread-forming property of the base is well controlled in this embodiment. Examples of the thread-reducing agent include polyethylene glycol and L-glutamic acid L-lysine.

There is no limitation on the active substance in percutaneously absorbable preparations of this invention. Examples of the active substances include drugs, physiologically active substances, cosmetics and nutrients. When drugs are employed as an active substance, especially poorly absorbable drugs through percutaneous route are good candidate. Examples of category of the percutaneously poorly absorbable drugs include peptides, proteins, nucleic acids, polysaccharides, other compounds of which molecular weight is larger than 1,000, and vaccines. Examples of peptides and proteins include physiologically active peptide/proteins such as insulin, calcitonin, erythropoietin (EPO), interferon, various interleukins, granulocyte colony-stimulating factors (G-CSF), vasopressin, desmopressin, urokinase, growth hormone, parathyroid hormone and grehelin. Examples of nucleic acids include vectors for gene therapy, anti-sense DNA, anti-sense RNA, and siRNA. Further, examples of vaccines include vaccines containing microorganism such as attenuated vaccines and inactivated vaccines, peptide vaccines, and nucleic acid vaccines such as DNA vaccines. Examples of polysaccharides include heparin and low molecular weight heparin.

Although there is no limitation in the content of the active substance in the percutaneously absorbable preparation of this invention, the content is generally 0.01-50 w/w %.

In a preferred embodiment, the base contains a stabilizer for stabilizing the active substance. Especially, when peptides or proteins are employed as an active substance, it is preferable to contain protease inhibitor as a stabilizer. Examples of the protease inhibitors include aprotinin and trypsin inhibitor. Further, when nucleic acids are employed as an active substance, it is preferable to contain nuclease inhibitor as a stabilizer.

In a further preferred embodiment, a moisture-proof layer is formed on the surface of the percutaneously absorbable preparations. For example, the moisture-proof layer is prepared by coating the surface with polymer solution like polyethylene glycol (PEG), polyvinylpyrolidone and polylactic acid, etc.

Figure 4A:
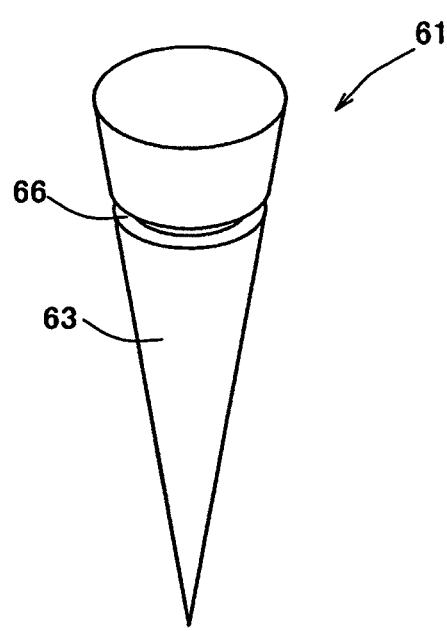
FIG. 4A is a perspective view showing an embodiment of the percutaneously absorbable preparations having a secant in all surroundings.
Figure 4B:
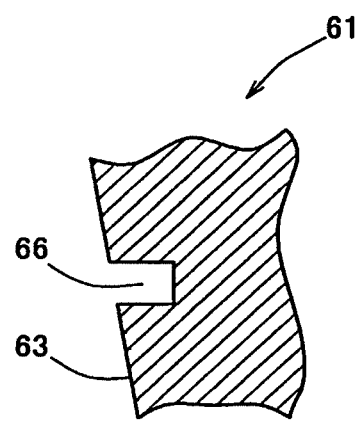
FIG. 4B is an enlarged sectional view of the part including the secant of FIG. 4A.
Figure 4C:
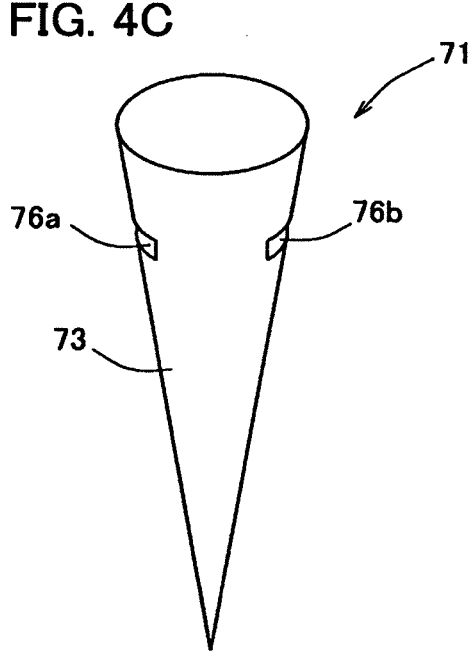
FIG. 4C is a perspective view showing an embodiment of the percutaneously absorbable preparations having a secant on a part of the surroundings.

In all embodiments of the above-mentioned percutaneously absorbable preparations, the surface is constricted or has a secant. More specifically, the dose of the administered active substance is made accurate by splitting along the constricted line or the secant after inserting the percutaneously absorbable preparations into the skin. The constricted line or the secant may be provided to all or a part of surroundings of the preparation. FIGS. 4A, 4B and 4C show embodiments of the percutaneously absorbable preparations having a secant. FIG. 4A is a perspective view showing an embodiment of the percutaneously absorbable preparations having a secant in all surroundings. FIG. 4B is an enlarged sectional view of the part including the secant of FIG. 4A. FIG. 4C is a perspective view showing an embodiment of the percutaneously absorbable preparations having a secant on a part of the surroundings. Percutaneously absorbable preparation 61 shown in FIG. 4A is prepared by providing preparation 1 shown in FIG. 1A with a secant. A secant 66 is made on a surface 63 in all surroundings. As shown in FIG. 4B, the secant 66 has a shape like a square groove. On the other hand, percutaneously absorbable preparation 71 as shown in FIG. 4C is prepared by providing preparation 1 shown in FIG. 1A with two secants. More specifically, secants 76a and 76b are made on mutually opposed portions on a surface 73. The shape of the secants 76a and 76b is the same as the secant 61 shown in FIG. 4B. The secants 76a and 76b in FIG. 4A, FIG. 4B and FIG. 4C are drawn in an exaggerated manner by the size and the size may be different from an actual size.

Figure 5:
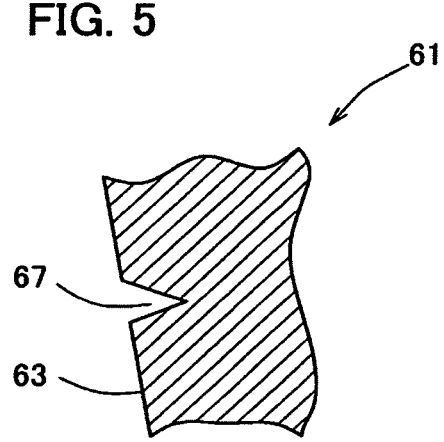
FIG. 5 is an enlarged sectional view of a constricted part of the percutaneously absorbable preparations.

In the percutaneously absorbable preparation 61 shown in FIG. 4A, an example of providing a constricted line instead of the secant 66 is shown in FIG. 5. FIG. 5 is an enlarged sectional view of a constricted part of the percutaneously absorbable preparations. As shown in FIG. 5, a constricted line 67 has a shape like a V-groove. Of course, as with the percutaneously absorbable preparation 61 shown in FIG. 4C, the constricted line 67 of FIG. 5 may be provided partially on the surface 63 instead of all surroundings on the surface 63. The constricted line 67 in FIG. 5 is drawn in an exaggerated manner by the size and the size may be different from an actual size.

Figure 6:
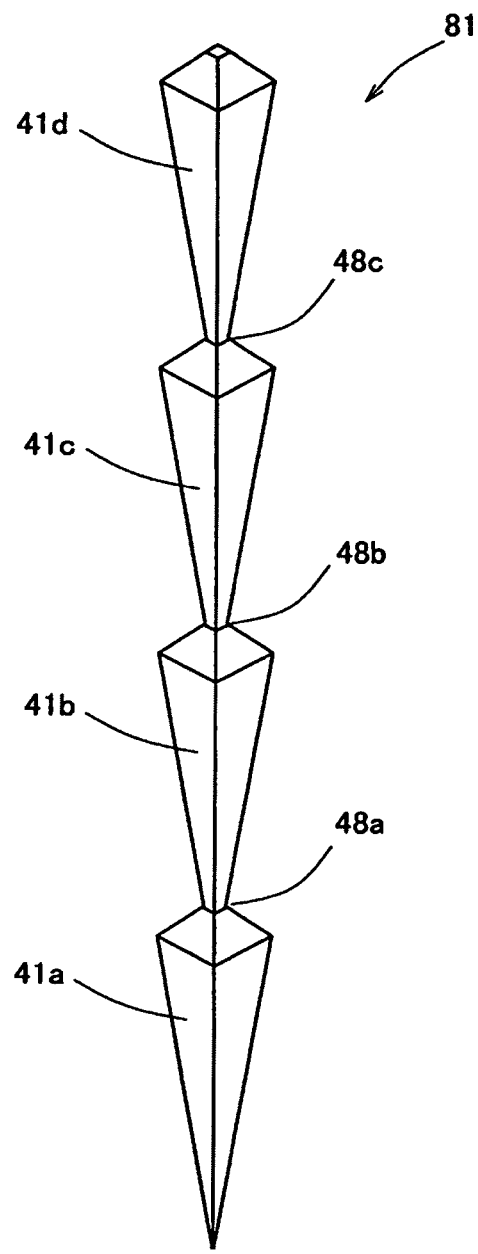
FIG. 6 is a perspective view showing an embodiment of the percutaneously absorbable preparations in the fifth aspect.

According to the fifth aspect of the invention, percutaneously absorbable preparations include at least two of percutaneously absorbable preparations of the first, second, third or fourth embodiment, wherein the preparations are linked in series. FIG. 6 is a perspective view showing an embodiment of the percutaneously absorbable preparations in the fifth aspect. In the percutaneously absorbable preparation 81 shown in FIG. 6, several percutaneously absorbable preparations shown in FIG. 2C are linked. More specifically, in the percutaneously absorbable preparation 81 shown in FIG. 6, four percutaneously absorbable preparations 41a-41d are linked in series, resulting in providing four connected parts 48a-48c. When the percutaneously absorbable preparation 81 is used, the part of the percutaneously absorbable preparation 41a is first inserted into the skin, and then cut at the connected part 48a. Next, the part of the percutaneously absorbable preparation 41b is inserted into another part on the skin, and then cut at the connected part 48b. Similarly, the steps of "insertion into the skin" and "cut at a connected part" are repeated. The four percutaneously absorbable preparations 41a-41d are continuously administered according to the percutaneously absorbable preparation 81 in this embodiment.

Figure 7A:
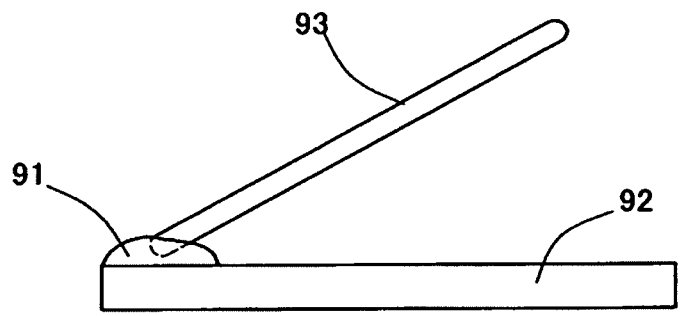
FIG. 7A is a side view schematically showing the initial stage of manufacturing process.
Figure 7B:
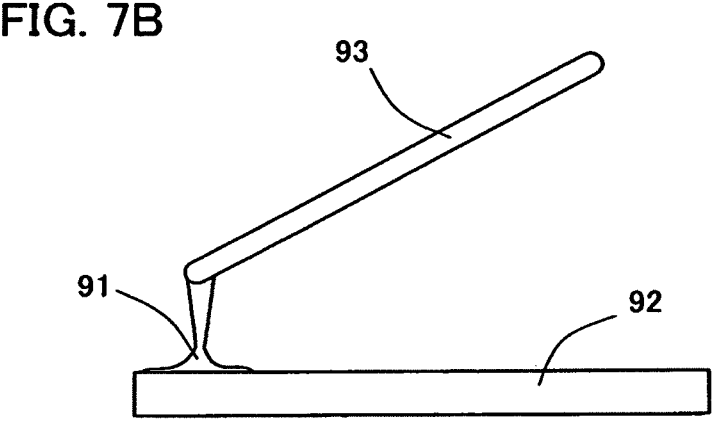
FIG. 7B is a side view schematically showing the midway stage thereof.
Figure 7C:
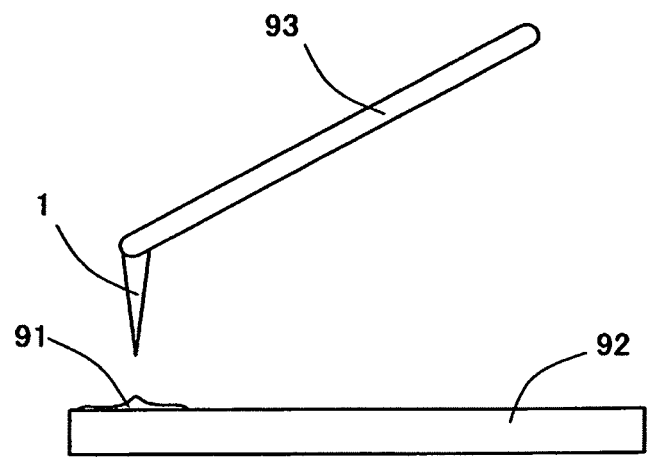
FIG. 7C is a side view schematically showing the final stage thereof.

Manufacturing methods of the percutaneously absorbable preparations of this invention will be described. Manufacturing methods of the percutaneously absorbable preparations of this invention are not limited particularly, and various methods are applicable. In an example, a plate and a stick are used. FIG. 7 schematically shows the manufacturing process of the invented percutaneously absorbable preparations. FIG. 7A is a side view schematically showing the initial stage of manufacturing process. FIG. 7B is a side view schematically showing the midway stage thereof. FIG. 7C is a side view schematically showing the final stage thereof. First of all, a base 91 that contains the objective substance is put on a plate 92 that consists of fluorocarbon resin etc. In this case, it is preferable that the substance which shows thread-forming property when dissolved with water is employed as the base to make it gluey. Next, the top of a glass stick 93 is in contact to the base 91 containing an active substance (FIG. 7A). The glass stick 93 is lifted at once, and the base 91 containing an active substance and adhering to the top of the glass stick 93 is elongated (FIG. 7B). In addition, the glass stick 93 is lifted, and the base 91 containing an active substance is formed into a needle-like or filamentous shape (FIG. 7C). Afterwards, percutaneously absorbable preparation 1 having about a cone shape is manufactured by drying or hardening the needle-like or filamentous shaped base 91 that contains the objective substance. At this time, a glass stick of which diameter is less than 5 mm can be used, for instance. Moreover, it does not limit to the glass stick, and a water-insoluble stick made of polypropylenes etc. is acceptable.

Figure 8A:
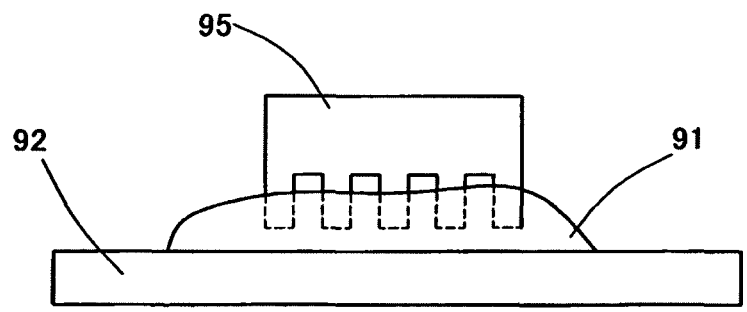
FIG. 8A is a side view schematically showing the initial stage of manufacturing process.
Figure 8B:
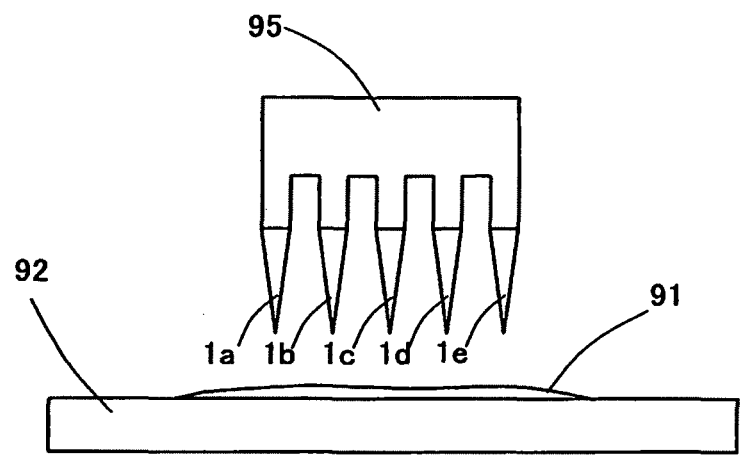
FIG. 8B is a side view schematically showing the final stage thereof.

Although FIGS. 7A-7C show an example of the manufacturing method of one percutaneously absorbable preparation, several percutaneously absorbable preparations can be manufactured by the same principle. An example of such a manufacturing method is shown in FIG. 8. FIG. 8 schematically shows another method to make percutaneously absorbable preparations of the invention. FIG. 8A is a side view schematically showing the initial stage of manufacturing process. FIG. 8B is a side view schematically showing the final stage thereof. As shown in FIG. 8A, a comb 95 having two or more projections instead of a stick is used in this example. Then, five percutaneously absorbable preparations 1a-1e are manufactured as shown in FIG. 8B through the same processes shown in FIGS. 7A-7C. Of course, it is also possible to manufacture more percutaneously absorbable preparations by increasing the number of projections of the comb 95.

Figure 9:
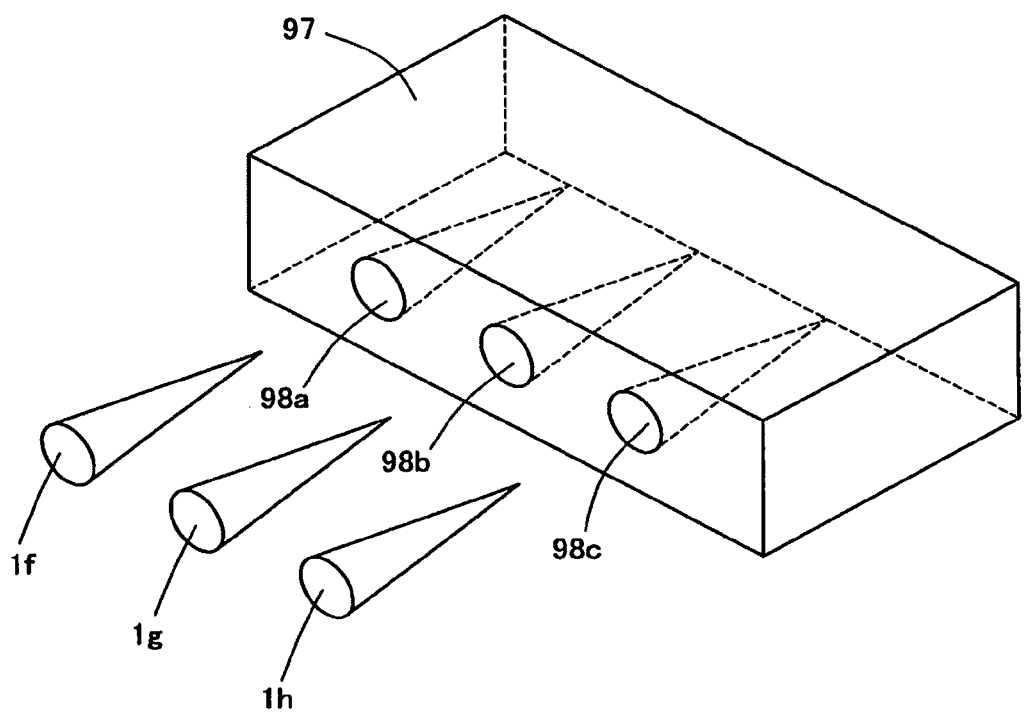
FIG. 9 is an exploded perspective schematic view showing another example of the process of manufacturing the percutaneously absorbable preparations of the invention.

A method using a mold is also applicable as another manufacturing method of percutaneously absorbable preparations of this invention. An example of the manufacturing process of the percutaneously absorbable preparations using mold is shown in FIG. 9. FIG. 9 is an exploded perspective schematic view showing another example of the process of manufacturing the percutaneously absorbable preparations of the invention. As shown in FIG. 9, a mold 97 is prepared by making conic holes 98a, 98b, and 98c in front of the plate 92 that consists of fluorocarbon resin etc. The base containing an objective substance is filled into these holes 98a, 98b, and 98c, and is removed after drying or hardening. As a result, needle-like or filamentous shape percutaneously absorbable preparations 1f, 1g and 1h are manufactured. If the base containing an active substance is gluey, it may be dried or hardened after removed from the holes. The material of the plate 92 is not limited to be fluorocarbon resin. For example, a plate made of silicon resin or ABS resins are acceptable.

Methods to make a constricted line or a secant on the percutaneously absorbable preparations of this invention are not limited particularly, and various methods are used. When a mold is used, a mold having a shape that can provide a constricted line or a secant is employed. When a plate and a stick are used, the constricted line or the secant is made, for instance, by pressing a desired point before drying or solidification process. Moreover, the constricted line or the secant is also made by shaving the desired point after drying or solidification process.

Figure 10:
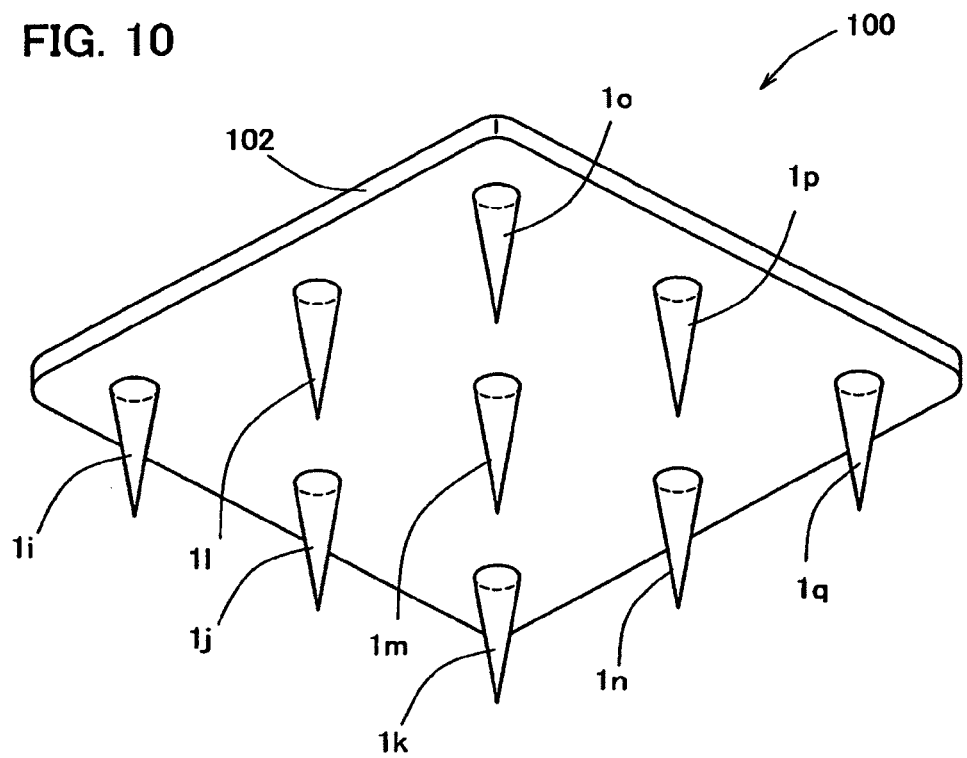
FIG. 10 is a perspective view showing an embodiment of a sheet-like carrier for holding the percutaneously absorbable preparations.

One aspect of a sheet-like carrier of the invention is a sheet-like carrier for holding at least one of the percutaneously absorbable preparations except the fifth aspect on at least one of the surfaces thereof, wherein the preparations held on the carrier are inserted into the skin by pushing the carrier thereonto. An embodiment of the sheet-like carrier of this aspect is shown in FIG. 10. FIG. 10 is a perspective view showing an embodiment of a sheet-like carrier for holding the percutaneously absorbable preparations. More specifically, a percutaneously absorbable preparations holding sheet-like carrier 100 in this embodiment consists of a sheet-like supporting body 102 and nine percutaneously absorbable preparations 1i-1q, and the nine percutaneously absorbable preparations 1i-1q are held on the one side of the supporting body 102. The nine percutaneously absorbable preparations 1i-1q are inserted into the skin by pushing the sheet-like carrier 100 onto the skin. After the sheet-like carrier 100 is pushed onto the skin, the supporting body 102 may be kept contact to the skin or only the supporting body 102 is removed from the skin. Although the sheet-like carrier 100 which holds nine percutaneously absorbable preparations 1i-1q is shown in FIG. 10, a sheet-like carrier of the present invention has no limitation on the number of percutaneously absorbable preparations, i.e. is allowed to hold one preparation only or, on the other hand, to hold more than 10 preparations. As the supporting body 102, conventional supporting bodies for use as a patch are used.

Figure 11A:
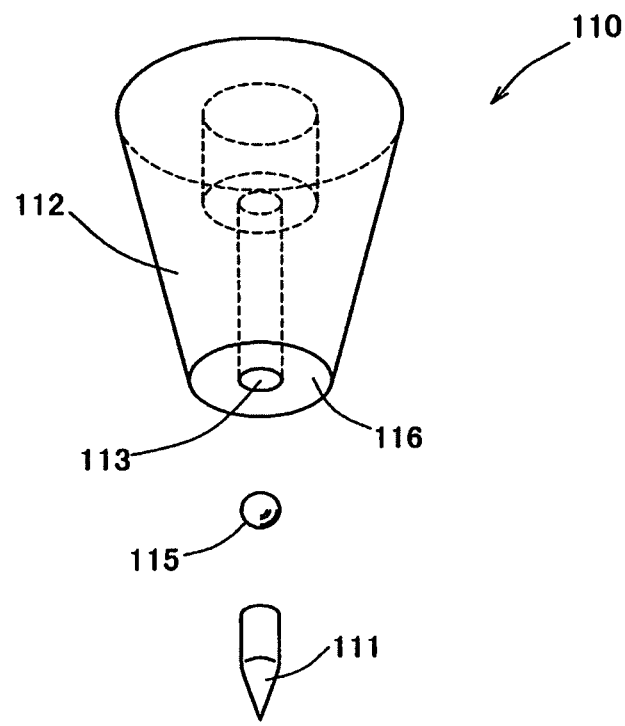
FIG. 11A is an exploded perspective view showing the first embodiment of the equipment of the invention.
Figure 11B:
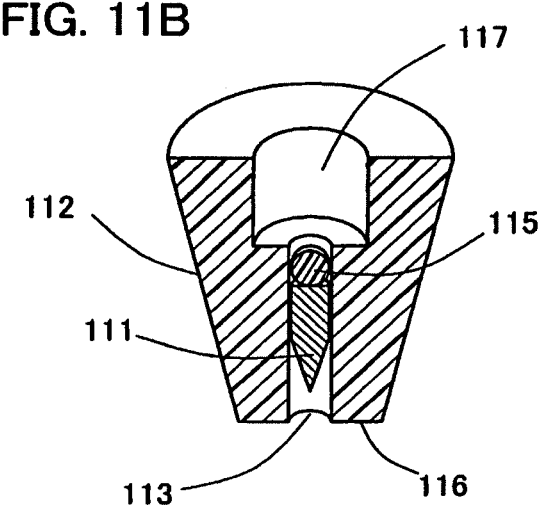
FIG. 11B is a sectional perspective view showing the first embodiment thereof.
Figure 12A:
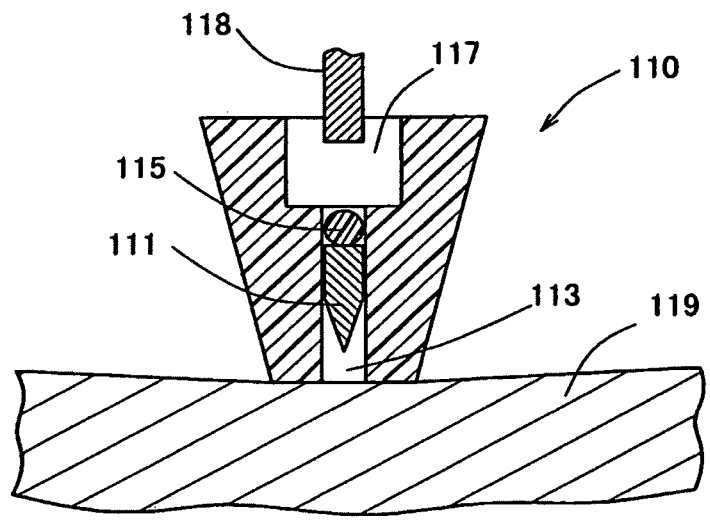
FIG. 12A is a schematic sectional view showing the pre-operation state of the equipment of FIG. 11.
Figure 12B:
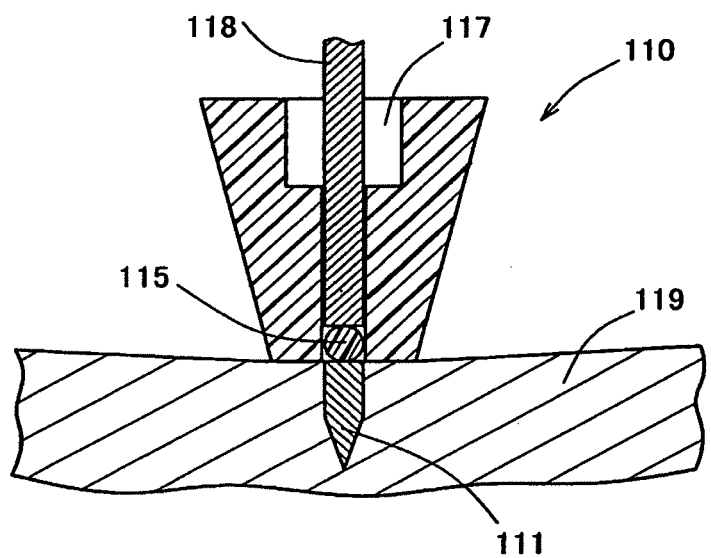
FIG. 12B is a schematic sectional view showing the post-operation state thereof.
Figure 13A:
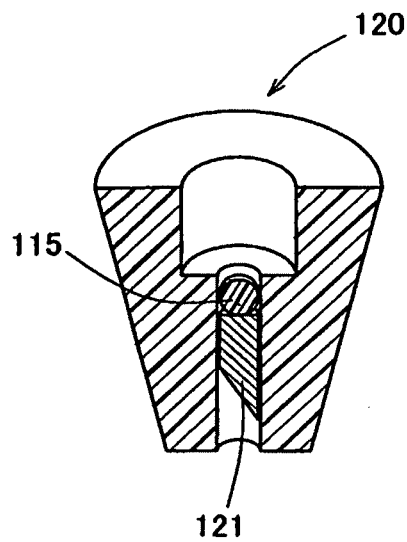
FIG. 13A is a sectional view showing the second embodiment of the equipment of the invention.
Figure 13B:
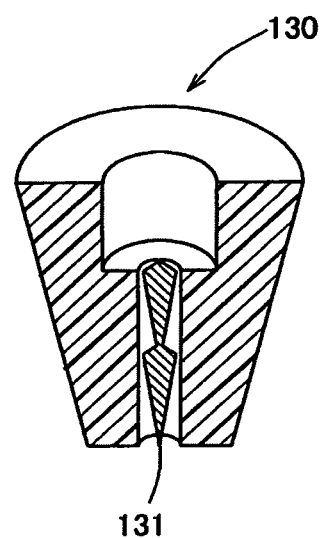
FIG. 13B is a sectional view showing the third embodiment of the equipment of the invention.
Figure 14:
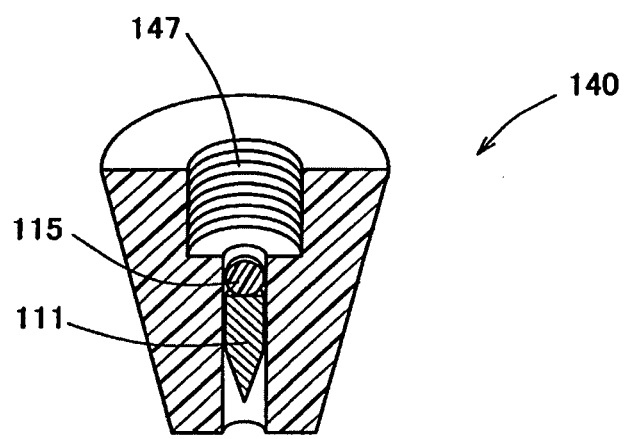
FIG. 14 is a sectional view showing the fourth embodiment of the equipment of the invention.
Figure 15:
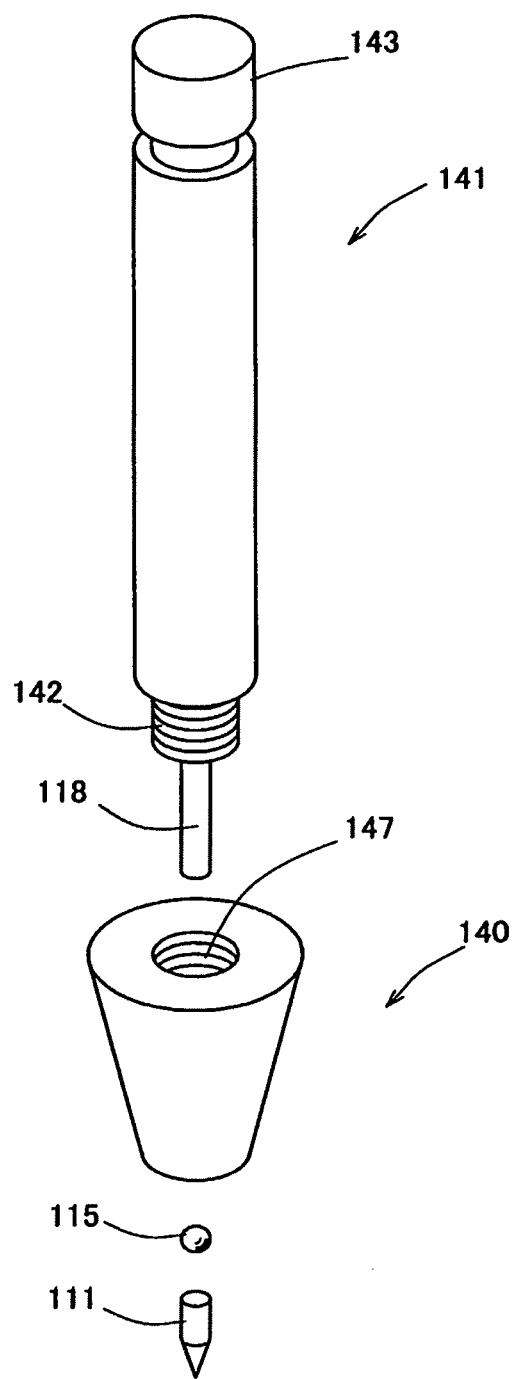
FIG. 15 is an exploded perspective view showing the positional relations between the pushing unit and the equipment in the fourth embodiment.

One aspect of equipment of the invention is equipment for holding percutaneously absorbable preparations including having a base of water-soluble and biologically soluble polymer material, an active substance held in the base, and having a slender, pointed shape, such as a needle-like or filamentous shape, adapted for insertion into skin to percutaneously administer the active substance into the body, the equipment including a main body having a penetration hole in and along which the preparations are moved. Embodiments of the equipment in this aspect are described with reference to FIGS. 11A-11B, 12A-12B and 13. FIGS. 11A and 11B show the first embodiment of the equipment of the invention. FIG. 11A is an exploded perspective view showing the first embodiment of the equipment of the invention. FIG. 11B is a sectional perspective view showing the first embodiment thereof. FIGS. 12A and 12B schematically show the pre- and post-operation states of the equipment of FIG. 11. FIG. 12A is a schematic sectional view showing the pre-operation state of the equipment of FIG. 11. FIG. 12B is a schematic sectional view showing the post-operation state thereof. FIGS. 13A and 13B show other embodiments of the equipment of the invention. FIG. 13A is a sectional view showing the second embodiment of the equipment of the invention. FIG. 13B is a sectional view showing the third embodiment of the equipment of the invention. FIG. 14 is a sectional view showing the fourth embodiment of the equipment of the invention. FIG. 15 is an exploded perspective view showing the positional relations between the pushing unit and the equipment in the fourth embodiment.

As shown in FIG. 11A, percutaneously absorbable preparations holding equipment 110 is composed of a main body 112 made of plastic, a bead 115 (spacer) and a percutaneously absorbable preparation 111. A penetration hole 113, which leads up and down, is installed in the main body 112, and the bead 115 and the percutaneously absorbable preparation 111 are held in the penetration hole 113. The bead 115 and the percutaneously absorbable preparation 111 move in and along the penetration hole 113. In addition, the bead 115 comes in contact with the percutaneously absorbable preparation 111. The outer shape of the main body 112 is like a truncated cone. Its large diameter is about 20 mm, its small diameter is about 10 mm, and its height is about 20 mm. Percutaneously absorbable preparation 111 is a preparation of either of the above described first to fourth embodiments. Percutaneously absorbable preparation 111 has the similar shape as percutaneously absorbable preparation 21 shown in FIG. 2A. Its diameter is about 0.2 mm, and its length is about 1.0 mm. The bead 115 is a spheroidal member, and its diameter is almost the same as the diameter of the percutaneously absorbable preparation 111. The bead 115 is made of silicon, but glass, resin and metal etc. are also acceptable. In addition, the percutaneously absorbable preparations holding equipment 110 has a skin contact surface 116 on the small diameter side. The skin contact surface 116 comes in contact with the skin when the percutaneously absorbable preparation 111 is used. Moreover, as shown in FIG. 11B, the main body 112 has a concave 117 to which an end of the penetration hole 113 is open. The concave 117 is made so that a pushing unit for pushing out the percutaneously absorbable preparation 111 via the bead 115 is smoothly installed. In FIGS. 11A and 11B, to facilitate the understanding, the size of the percutaneously absorbable preparation 111 and the penetration hole 113 is drawn as an enlarged manner.

As shown in FIG. 12A, the bead 115 and the percutaneously absorbable preparation 111 are stored in penetration hole 113 in the pre-operation state of the equipment 110. When it is used, one side of the bead 115 is pushed from the side of the concave 117 of the percutaneously absorbable preparations holding equipment 110. The bead 115 comes in contact with the percutaneously absorbable preparation 111, and then, the percutaneously absorbable preparation 111 is pushed via the bead 115. In this embodiment, one side of the bead 115 is pushed with a wire 118. The wire 118 is made of stainless steel and has almost the same diameter as the bead 115. As shown in FIG. 12B, the percutaneously absorbable preparation 111 is completely pushed out by the wire 118 via the bead 115 and is inserted into the skin 119. At this time, the wire 118 does not come in contact with the skin 119, because it works via the bead 115. More specifically, the wire 118 is not polluted by the body fluid secreted from the skin 119. In FIGS. 12A and 12B, to facilitate the understanding, the sizes of the percutaneously absorbable preparations 111, the penetration hole 113, the bead 115, and the wire 118 are drawn as an enlarged manner.

In the percutaneously absorbable preparations holding equipment 110, another shape of the held percutaneously absorbable preparations is acceptable. Percutaneously absorbable preparations holding equipment 120 as shown in FIG. 13A holds a percutaneously absorbable preparation 121 having a filamentous shape. The percutaneously absorbable preparation 121 has almost the similar shape as the percutaneously absorbable preparation 51 of FIG. 3, and the size is almost the same as that of the percutaneously absorbable preparation 111. On the other hand, percutaneously absorbable preparations holding equipment 130 shown in FIG. 13B holds a percutaneously absorbable preparation 131 having two percutaneously absorbable preparations 41, shown in FIG. 2C, linked in series. According to the percutaneously absorbable preparations holding equipment 130, half of the percutaneously absorbable preparation 131 is repeatedly administered at two times.

Female threads are formed in a concave 147 of percutaneously absorbable preparations holding equipment 140 shown in FIG. 14. The percutaneously absorbable preparations holding equipment 140 in this embodiment is used by installing it to a pushing unit 141 shown in FIG. 15. The pushing unit 141 has the wire 118, and the wire 118 moves at a constant distance by pushing a knock part 143. Moreover, the pushing unit 141 has a convex part 142 that engages with the concave 147 of the percutaneously absorbable preparations holding equipment 140. Male threads are made in just fit to the female threads formed in the concave 147 in the convex part 142. As the pushing unit 141, for example, a mechanical pencil for writing is applicable. More specifically, a mechanical pencil becomes useful as the pushing unit 141 by using the wire 118 instead of an extra lead, wherein the diameter of the wire 118 is the same as that of the extra lead. Moreover, the pushing unit 141 can be made by using the mechanism of a knock-type ballpoint pen. In FIGS. 13A, 13B, 14 and 15, to facilitate the understanding, the sizes of the percutaneously absorbable preparations 111, 121, 131, bead 115, and the wire 118 are drawn as an enlarged manner.

As mentioned above, the percutaneously absorbable preparations holding equipments 110, 120, 130 and 140 are mainly used as if it were a cartridge of percutaneously absorbable preparations. A required number of percutaneously absorbable preparations holding equipments 110, 120, 130 and 140 are used by breaking the package when the equipments are packaged piece by piece. Consequently, they are kept hygienic.

The following provides a more detailed explanation of the present invention through its examples, though this invention is not limited with these examples.

Example 1

This example illustrates a percutaneously absorbable preparation having a needle-like and filamentous shape and containing interferon (active substance) held in a base consisting of human serum albumin.

About 0.2 mL of distilled water was added to 150 mg of human serum albumin (Sigma) to be dissolved. The solution was mixed well to give a gluey base consisting of human serum albumin. To this base, 10 μL of interferon alpha injection solution "Sumiferon" (Trademark, 6,000,000 units/mL, Sumitomo pharmaceuticals), corresponding to 60,000 IU, was added and well mixed so that interferon was held in the base. To the gluey base holding interferon, a top of a glass stick of which diameter was about 3 mm was attached. Thereafter, the top was gradually pulled apart to form the base into a needle-like or filamentous shape. It was then solidified by drying at low temperature to give a percutaneously absorbable preparation having a needle-like or filamentous shape.

Mice, about 30 g body weight, were fixed on an operating table after the abdominal hair was shaved under anesthetized with pentobarbital. At this point, about 0.25 mL blood sample was at first collected from the jugular vein. Next, the percutaneously absorbable preparation made in this example was inserted into the shaved abdominal skin of mice, and interferon was administered percutaneously, wherein the dose of interferon was 10,000 IU/kg. Blood samples were collected from the jugular vein for 4 hr after administration. Serum sample was prepared from the obtained each blood sample, and interferon concentration of each serum sample was measured with ELISA. All data were calculated as the mean+/− standard deviation (SD), wherein each group consists of three to four mice. The results are shown in Table 1. "ND" shows the concentration below the detection limit (as the same as the following tables). As a result, interferon concentration started to increase at 1 hr after administration and showed its maximum concentration (22.9+/−7.9 IU/mL) at 3 hr after administration. Therefore, it was shown that interferon was administered percutaneously with the percutaneously absorbable preparation of this example.

TABLE 1

| Elapsed time after administration (hr) | before administration | 1 | 2 | 3 | 4 |
|---|---|---|---|---|---|
| Interferon concentration (IU/mL) | ND | 5.8 ± 3.8 | 19.3 ± 8.5 | 22.9 ± 7.9 | 17.7 ± 3.4 |

Example 2

This example illustrates a percutaneously absorbable preparation having a needle-like and filamentous shape and containing interferon (active substance) held in a base consisting of bovine serum α-acid glycoprotein (AAG).

About 50 μL of distilled water was added to 50 mg of bovine AAG (Sigma) to be dissolved. The solution was mixed well and water was evaporated to give a base paste consisting of AAG. To this base paste, 10 μL of interferon alpha injection solution "Sumiferon" (Trademark, 6,000,000 units/mL, Sumitomo pharmaceuticals), corresponding to 60,000 IU, was added and well mixed so that interferon was held in the base paste. A Percutaneously absorbable preparation having a needle-like or filamentous shape was made with a glass stick in the same way as Example 1.

Example 3

This example illustrates a percutaneously absorbable preparation having a needle-like and filamentous shape and containing FITC-labeled albumin (active substance) held in a base consisting of human serum albumin. FITC-labeled albumin was used as a model of vaccine.

FITC-labeled albumin was prepared by labeling human serum albumin with fluorescein isothiocyanate (FITC). On the other hand, about 0.2 mL of distilled water was added to 130 mg of human serum albumin (Sigma) to be dissolved. The solution was mixed well to give a base paste consisting of human serum albumin. To this base paste, 20 mg of FITC-labeled albumin was added and well mixed, so that FITC-labeled albumin was held in the base paste. To the base paste holding FITC-labeled albumin, a top of a polypropylene stick of which diameter was about 2 mm was attached. Thereafter, the top was gradually pulled apart so that the base paste attaching to the top has a needle-like or filamentous shape. The needle-like or filamentous base paste was solidified by drying at low temperature to give a percutaneously absorbable preparation having a needle-like or filamentous shape.

Mice, about 30 g body weight, were fixed on an operating-table after the abdominal hair was shaved under anesthetized with pentobarbital. At this point, about 0.25 mL blood was at first collected from the jugular vein. Next, five percutaneously absorbable preparations prepared in this example were inserted into the mice abdominal skin, and FITC-labeled albumin was administered percutaneously. Whole blood was removed in the next day and serum sample was prepared from the resulting blood. Each serum sample was diluted at 20 times with distilled water and the fluorescent intensity was measured with spectrofluorometer with the excitation wavelength of 490 nm and emission one of 510 nm. As a result, the serum sample obtained after administration showed 20 times stronger fluorescent intensity than that obtained before administration. From these results, it was shown that FITC-labeled albumin as a model vaccine was administered percutaneously.

Example 4

This example illustrates a percutaneously absorbable preparation having a needle-like and filamentous shape and containing insulin (active substance) held in a base consisting of sodium chondroitin sulfate C.

About 0.1 mL of distilled water was added to 200 mg of sodium chondroitin sulfate C (Nacalai Tesque) to be dissolved. The solution was mixed well under warm to give a base paste consisting of sodium chondroitin sulfate C. After cooled to the room temperature, 10 µL, of sodium insulin solution (100 mg/mL, private processed product) was added to this base paste and well mixed so that insulin was held in the base paste. To the paste base holding insulin, a top of a polypropylene stick of which diameter was about 3 mm was attached. Thereafter, the top was gradually pulled apart so that the base paste attaching to the top has a needle-like or filamentous shape. In addition, a secant was made on the surface of the needle-like or filamentous base paste with a wire of which diameter was 20 µm. The needle-like or filamentous base paste with the secant was solidified by drying at low temperature to give a percutaneously absorbable preparation having a needle-like or filamentous shape.

The percutaneously absorbable preparation made in this example was evaluated by means of hypoglycemic effect in mice. Mice, about 30 g body weight, were anesthetized by an injection of pentobarbital and were fixed on the operating-table after the hair of the abdomen was shaved. At this point, about 0.25 mL blood was at first collected from the jugular vein. Next, five percutaneously absorbable preparations (corresponding to 1.0 IU/kg) made in this example was inserted into the shaved abdomen, and insulin was administered percutaneously. Blood samples were collected from the jugular vein for 3 hr after administration. Serum samples were obtained from the obtained blood samples and glucose content in each serum sample was measured using glucose assay kit (Glucose C II-Test kit, Wako Pure Chemical Industries). Each glucose level was shown as a relative value to the pre-dose level, 100%. All data were calculated as the mean+/− standard deviation (SD), where each group consisting of three to four mice. The results are shown in Table 2. As a result, serum glucose level showed its minimum value within 1 hr after administration, and the effect of insulin was confirmed. From these results, it was shown that insulin was administered percutaneously by the percutaneously absorbable preparation of this example.

TABLE 2

| Elapsed time after administration (hr) | before administration | 1 | 2 | 3 | 4 |
|---|---|---|---|---|---|
| Glucose level (%) | 100 | 28 ± 8 | 35 ± 11 | 62 ± 9 | 77 ± 8 |

Example 5

This example illustrates a percutaneously absorbable preparation having a needle-like and filamentous shape and containing insulin (active substance) held in a base consisting of dextrin.

About 1 mL of distilled water was added to 2 g of dextrin (Wako Pure Chemical Industries) to be dissolved. The solution was mixed well with motor and pestle to give a base paste consisting of dextrin. Ten µL of sodium insulin solution (100 mg/mL, private processed product) was added to 100 mg of this base paste and well mixed so that insulin was held in the base paste. To the base paste holding insulin, a top of a glass stick of which diameter was about 3 mm was attached. Thereafter, the top was gradually pulled apart so that the base paste attaching to the top has a needle-like or filamentous shape. In addition, a secant was made on the surface of the needle-like or filamentous base paste with a wire of which diameter was 20 µm. The needle-like or filamentous base paste with the secant was solidified by drying at low temperature to give a percutaneously absorbable preparation having a needle-like or filamentous shape.

Animal experiments using mice were performed in the same way as Example 4. Table 3 shows the result. As a result, serum glucose level showed its minimum value within 1 hr after administration, and the effect of insulin was confirmed. From these results, it was shown that insulin was administered percutaneously by the percutaneously absorbable preparation of this example.

TABLE 3

| Elapsed time after administration (hr) | before administration | 1 | 2 | 3 | 4 |
|---|---|---|---|---|---|
| Glucose level (%) | 100 | 21 ± 6 | 30 ± 7 | 56 ± 8 | 63 ± 7 |

Example 6

This example illustrates a percutaneously absorbable preparation having a needle-like and filamentous shape and containing erythropoietin (active substance) held in a base consisting of hydroxypropyl cellulose.

About 1 mL of distilled water was added to 2 g of hydroxypropyl cellulose (L-HPC, Nippon Soda) to be dissolved. The solution was mixed well with motor and pestle to give a base paste consisting of hydroxypropyl cellulose. Ten µL of erythropoietin EPO injection "ESPO" (Trademark, 24,000 IU/mL, Kirin Breweries) was added to 100 mg of this base paste and well mixed so that erythropoietin was held in the base paste. To the base paste holding erythropoietin, a top of a glass stick of which diameter was about 3 mm was attached. Thereafter, the top was gradually pulled apart so that the base paste attaching to the top has a needle-like or filamentous shape. The needle-like or filamentous base paste was solidified by drying at low temperature to give a percutaneously absorbable preparation having a needle-like or filamentous shape.

Mice, about 30 g body weight, were anesthetized by an injection of pentobarbital and were fixed on the operating-table after the hair of the abdomen was shaved. The percutaneously absorbable preparation made in this example was inserted into the shaved abdomen, and erythropoietin was administered percutaneously, wherein the dose was 100 IU/kg. Blood samples were collected from the jugular vein before and after administration for 5 hr. Serum samples were obtained from the obtained blood samples and erythropoietin concentrations were measured by an ELISA method. Table 4 shows the result. That is, erythropoietin concentration started to increase at 1 hr after administration and kept rising until 5 hr. From these results, it was shown that erythropoietin was administered percutaneously by the percutaneously absorbable preparation of this example.

TABLE 4

| Elapsed time after administration (hr) | before administration | 1 | 2 | 3 | 4 | 5 |
| --- | --- | --- | --- | --- | --- | --- |
| Erythropoietin concentration (IU/mL) | ND | 8 ± 4 | 11 ± 5 | 18 ± 6 | 26 ± 5 | 36 ± 5 |

Example 7

This example illustrates a percutaneously absorbable preparation having a needle-like and filamentous shape and containing insulin (active substance) held in a base consisting of human serum albumin and hydroxypropyl cellulose.

About 0.2 mL of distilled water was added to 150 mg of human serum albumin and 25 mg of hydroxypropyl cellulose (L-HPC, Nippon Soda) to be dissolved. The solution was mixed well to give a base paste consisting of human serum albumin and hydroxypropyl cellulose. Ten μL of sodium insulin solution (100 mg/mL, private processed product) was added to 100 mg of this base paste and well mixed so that insulin was held in the base paste. To the base paste holding insulin, a top of a polypropylene stick of which diameter was about 2 mm was attached. Thereafter, the top was gradually pulled apart so that the base paste attaching to the top has a needle-like or filamentous shape. In addition, a wire of 20 μm in the diameter was attached to a part of the surface of the needle-like or filamentous base, where the part is near the boundary between the base and the top, and a constricted line for cut was made by rotating the wire. The needle-like or filamentous base paste with the constricted line was solidified by drying at low temperature to give a percutaneously absorbable preparation having a needle-like or filamentous shape.

Example 8

This example illustrates a percutaneously absorbable preparation on which moisture-proof layer was formed with polyethylene glycol, wherein the preparation has a needle-like and filamentous shape and contains insulin (active substance) held in a base consisting of dextrin.

About 1.0 mL of distilled water was added to 2 g of dextrin (Wako Pure Chemical Industries) to be dissolved. The solution was mixed well with motor and pestle to give a base paste consisting of dextrin. Ten μL of sodium insulin solution (100 mg/mL, private processed product) was added to 100 mg of this base paste and well mixed so that insulin was held in the base paste. To the base paste holding insulin, a top of a glass stick of which diameter was about 3 mm was attached. Thereafter, the top was gradually pulled apart so that the base paste attaching to the top has a needle-like or filamentous shape. In addition, a wire of 20 μm in the diameter was attached to a part of the surface of the needle-like or filamentous base, where the part is near the boundary between the base and the top, and a constricted line for cut was made by rotating the wire. The needle-like or filamentous base with the constricted line was solidified by drying at low temperature to give a solid preparation having a needle-like or filamentous shape. On the other hand, methylene chloride solution containing 5% of polyethylene glycol 20000 (PEG20000, Nacalai Tesque) was made. The obtained solid preparation having a needle-like or filamentous shape was soaked in this solution at the position of the constricted line and coating on the surface of the solid preparation was performed with PEG 20,000 after drying in air. Thus, a percutaneously absorbable preparation having a needle-like and filamentous shape and having moisture-proof layer on its surface was prepared.

Example 9

This example illustrates a percutaneously absorbable preparation on which moisture-proof layer was formed with polyethylene glycol, wherein the preparation has a needle-like and filamentous shape and contains insulin (active substance) held in a base consisting of gelatin and dextrin.

About 3 mL of distilled water was added to 3 g of gelatin (Wako Pure Chemical Industries) and 0.8 g of dextrin (Wako Pure Chemical Industries) to be dissolved. The solution was mixed well at about 50° C. with motor and pestle to give a base paste consisting of gelatin and dextrin. Ten μL of sodium insulin solution (100 mg/mL, private processed product) was added to 100 mg of this base paste and well mixed so that insulin was held in the base paste. Thereafter, a needle-like and filamentous solid preparation with a constricted line was obtained in the same way as Example 8. In addition, the surface of the solid preparation was coated with PEG 20000 in the same way as Example 8. Thus, a percutaneously absorbable preparation having a needle-like and filamentous shape and having moisture-proof layer on its surface was prepared.

Example 10

This example illustrates a percutaneously absorbable preparation having a needle-like and filamentous shape, containing insulin (active substance) held in a base consisting of gelatin and dextrin, and further containing soybean trypsin inhibitor (stabilizer).

About 3 mL of distilled water was added to 3 g of gelatin (Wako Pure Chemical Industries), 0.8 g of dextrin (Wako Pure Chemical Industries) and 1 mg of soybean trypsin inhibitor (Sigma) to be dissolved. The solution was mixed well at about 40° C. with motor and pestle to give a base paste consisting of gelatin and dextrin and containing soybean trypsin inhibitor. Ten μL of sodium insulin solution (100 mg/mL, private processed product) was added to 100 mg of this base paste and well mixed so that insulin was held in the base paste. On the other hand, a mold having a needle-like or filamentous shape was made by inserting a sewing needle into a plate made of perfluoroalkoxy (PFA) resin with a hammer. The base paste holding insulin was introduced into this mold at 40° C. The introduced base paste was solidified by cooling after left at room temperature to give a solid preparation. The solid preparation was removed from the mold to give a percutaneously absorbable preparation having a needle-like or filamentous shape.

Example 11

This example illustrates a percutaneously absorbable preparation having a needle-like and filamentous shape, containing low molecular weight heparin (active substance) held in a base consisting of sodium chondroitin sulfate C, and further containing PEG 20,000 (thread-reducing agent) and caprylic acid (absorption enhancer).

Fifty μL of 5% PEG 20,000 (Nacalai Tesque) solution was added to 100 mg of sodium chondroitin sulfate C (Nacalai Tesque) to be dissolved. The solution was mixed well with motor and pestle to give a base paste consisting of chondroitin sulfate C and containing PEG 20,000. To this base, 5 mg of low molecular weight heparin (Parnaparin) and 5 mg of capric acid (Wako Pure Chemical Industries) were added and well mixed so that low molecular weight heparin and capric acid were held in the base paste. To this base paste holding low molecular weight heparin and capric acid, a top of a glass stick of which diameter was about 2 mm was attached. Thereafter, the top was gradually pulled apart so that the base paste attaching to the top has a needle-like or filamentous shape. In addition, a secant was made on the surface of the needle-like or filamentous base paste with a wire of which diameter was 20 μm. The needle-like or filamentous base paste with the secant was solidified by drying at low temperature to give a percutaneously absorbable preparation having a needle-like or filamentous shape. Evaluation in animal experiment using mice was performed as the same method as Example 12 after-described.

Example 12

This example illustrates a percutaneously absorbable preparation which was the same as that of Example 11 but does not have a secant.

A base paste consisting of sodium chondroitin sulfate C and containing PEG 20,000 was prepared in the same way as Example 11. Further, low molecular weight heparin and capric acid were held in the base paste in the same way as Example 11. To this base paste holding low molecular weight heparin and capric acid, a top of a glass stick of which diameter was about 3 mm was attached. Thereafter, the top was gradually pulled apart so that the base paste attaching to the top has a needle-like or filamentous shape. The needle-like or filamentous base paste was solidified by drying at low temperature to give a percutaneously absorbable preparation having a needle-like or filamentous shape.

As a comparative example against Examples 11 and 12, a percutaneously absorbable preparation which was the same as that of Example 11 but does not contain caprylic acid was made.

Mice, about 30 g body weight, were anesthetized by an injection of pentobarbital and were fixed on the operating-table after the hair of the abdomen was shaved. Percutaneously absorbable preparations made in Example 11, Example 12 and comparative examples were inserted into the shaved abdominal skin respectively, and low molecular weight heparin was administered percutaneously. The dose was 100 IU/kg. Blood samples were collected from the jugular vein for 4 hr after administration. Blood samples were obtained. Serum sample was prepared from the obtained each blood sample, and heparin activity (anti-Xa activity) of each sample was measured with Hemos IL™ Assay Kit (Instrumentation Laboratory, United States). Table 5 shows the result. With the percutaneously absorbable preparations of Examples 11 and 12, anti-Xa activity started to increase at 1 or 2 hr after administration and showed the maximum value at 3 hr after administration. On the other hand, in the percutaneously absorbable preparations of comparative example, anti-Xa activity was not detected even at 4 hr after administration. Therefore, when the low molecular weight heparin is the active substance, it was shown that an absorption enhancer such as caprylic acid was necessary.

TABLE 5

| Elapsed time after administration (hr) | | before administration | 1 | 2 | 3 | 4 |
|---|---|---|---|---|---|---|
| Anti-Xa activity (IU/mL) | Example 11 | ND | ND | 0.13 ± 0.05 | 0.21 ± 0.08 | 0.19 ± 0.05 |
| | Example 12 | ND | 0.12 ± 0.04 | 0.19 ± 0.07 | 0.20 ± 0.08 | 0.17 ± 0.07 |
| | Comparative example | ND | ND | ND | ND | ND |

Example 13

This example illustrates a percutaneously absorbable preparation having a needle-like and filamentous shape and containing interferon (active substance) held in a base consisting of glycogen.

About 1 mL of distilled water was added to 1 g of glycogen (Nacalai Tesque) to be dissolved. The solution was mixed well under warm to give a base paste consisting of glycogen. To this base, 10 μL of interferon alpha injection solution "Sumiferon" (Trademark, 6,000,000 units/mL, Sumitomo Pharmaceuticals) corresponding to 60,000 IU was added and well mixed so that interferon was held in the base paste. To this base paste holding interferon, a top of a glass stick of which diameter was about 3 mm was attached. Thereafter, the top was gradually pulled apart so that the base paste attaching to the top has a needle-like or filamentous shape. The needle-like or filamentous base paste was solidified by drying at low temperature to give a percutaneously absorbable preparation having a needle-like or filamentous shape.

Example 14

This example illustrates a percutaneously absorbable preparation having a needle-like and filamentous shape, containing insulin (active substance) held in a base consisting of carboxyvinyl polymer, and further containing PEG 20,000 (thread-reducing agent).

Two mL of 1% PEG 20,000 (Nacalai Tesque) solution was added to 3 g of carboxyvinyl polymer (Nacalai Tesque) to be dissolved. The solution was mixed well to give a base paste consisting of carboxyvinyl polymer and containing PEG 20,000. To 100 mg of this base paste, 10 μL of sodium insulin solution (100 mg/mL, private processed product) was added and well mixed so that insulin was held in the base paste. To this base paste, a top of a polypropylene stick of which diameter was about 3 mm was attached. Thereafter, the top was gradually pulled apart so that the base paste attaching to the top has a needle-like or filamentous shape. After a constricted line for cut was made in the same way as Example 8, the needle-like or filamentous base paste with the constricted line was solidified by drying at low temperature to give a percutaneously absorbable preparation having a needle-like or filamentous shape.

Example 15

This example illustrates a percutaneously absorbable preparation having a needle-like and filamentous shape and containing vitamin C (active substance) held in a base consisting of dextran and hyaluronic acid.

About 50 μL of distilled water was added to 80 mg of dextran (molecular weight 170,000-200,000, Nacalai Tesque), 2 mg of hyaluronic acid (mean molecular weight 90,000, commodity code: FCH-SU, Kibun Food Chemifa Co.) and 5 mg of vitamin C (L-ascorbic acid, Wako Pure Chemical Industries) to be dissolved. The solution was mixed well to give a base paste consisting of dextran and hyaluronic acid and holding vitamin C. To this base paste holding vitamin C, a top of a glass stick of which diameter was about 3 mm was attached. Thereafter, the top was gradually pulled apart so that the base paste attaching to the top has a needle-like or filamentous shape. The needle-like or filamentous base paste was solidified by drying at low temperature to give a percutaneously absorbable preparation having a needle-like or filamentous shape.

Example 16

This example illustrates a percutaneously absorbable preparation having a needle-like and filamentous shape and containing vitamin C (active substance) held in a base consisting of pullulan and hyaluronic acid.

About 50 μL of distilled water was added to 50 mg of pullulan (commodity code: PI-20, Hayashibara Shoji, Inc.), 1 mg of hyaluronic acid (mean molecular weight 90,000, commodity code: FCH-SU, Kibun Food Chemifa Co.) and 2 mg of vitamin C (L-ascorbic acid, Wako Pure Chemical Industries) to be dissolved. The solution was mixed well to give a base paste consisting of pullulan and hyaluronic acid and holding vitamin C. To this base paste holding vitamin C, a top of a glass stick of which diameter was about 3 mm was attached. Thereafter, the top was gradually pulled apart so that the base paste attaching to the top has a needle-like or filamentous shape. The needle-like or filamentous base paste was solidified by drying at low temperature to give a percutaneously absorbable preparation having a needle-like or filamentous shape.

Example 17

This example illustrates a percutaneously absorbable preparation having a needle-like and filamentous shape and containing low molecular weight heparin (active substance) held in a base consisting of human serum albumin.

About 0.2 mL of distilled water was added to 150 mg of human serum albumin to be dissolved. The solution was mixed well to give a base paste consisting of human serum albumin. To this base paste, 5 mg of low molecular weight heparin (Parnaparin) was added and well mixed so that low molecular weight heparin was held in the base paste. To this base paste, a top of a glass stick of which diameter was about 2 mm was attached. Thereafter, the top was gradually pulled apart so that the base paste attaching to the top has a needle-like or filamentous shape. The needle-like or filamentous base paste was solidified by drying in air to give a percutaneously absorbable preparation having a needle-like or filamentous shape.

Mice, about 30 g body weight, were anesthetized by an injection of pentobarbital and were fixed on the operating-table after the hair of the abdomen was shaved. A percutaneously absorbable preparation made in this example was inserted into the shaved abdominal skin respectively, and low molecular weight heparin was administered percutaneously. The dose was 100 IU/kg. Systemic blood samples were collected from the jugular vein for 6 hr after administration. Serum sample was prepared from the obtained each blood sample, and heparin activity (anti-Xa activity) of each sample was measured with Hemos IL™ Assay Kit (Instrumentation Laboratory, United States). Table 6 shows the result. That is, serum anti-Xa activities were lower than its level of quantitation, 0.1 IU/mL, before administration and at 1 hr after administration. Thereafter, anti-Xa activity increased gradually till 4 hr. Therefore, it was shown that low molecular weight heparin was administered percutaneously with a percutaneously absorbable preparation of this example.

TABLE 6

| Elapsed time after administration (hr) | before administration | 1 | 2 | 3 | 4 | 5 | 6 |
|---|---|---|---|---|---|---|---|
| Anti-Xa activity (IU/mL) | ND | ND | 0.13 | 0.21 | 0.18 | 0.14 | 0.11 |

Example 18

This example illustrates a percutaneously absorbable preparation having a needle-like and filamentous shape and containing low molecular weight heparin (active substance) held in a base consisting of human serum albumin, where the low molecular weight heparin was released with a sustained-released manner.

According to the same method as Example 17, a solid preparation having a needle-like or filamentous shape was obtained. On the other hand, 2 mL of 25% glutaraldehyde solution (Nacalai Tesque) was added to 10 mL of ethanol and was mixed well. To this mixture, the obtained solid preparation was soaked for 5 min and cross-linking treatment was performed on its surface. The treated solid preparation was soaked in ethanol and water for 30 sec, respectively and the surface was washed. The washed solid preparation was dried in air to give a percutaneously absorbable preparation having a needle-like or filamentous shape.

With the percutaneously absorbable preparation made in this example, dissolution experiment was performed for 5 hr at 37° C. Ten mL of dissolution test medium was prepared by diluting rat skin homogenate to ten times with isotonic phosphate buffer (pH7.4). The anti-Xa activity of the dissolution test medium was measured by using the above-mentioned Hemos IL™ Heparin Assay Kit. As a reference, the percutaneously absorbable preparation made in Example 17 was used and the same study was performed. Table 7 shows the result. That is, the anti-Xa activity was not detected until 10 min after the start of the dissolution experiment. At 30 min after the start of the experiment, anti-Xa activity was initially detected. Moreover, anti-Xa activity showed high values at 3 hr after the start of the experiment. On the other hand, in the case of the percutaneously absorbable preparation made in Example 17, anti-Xa activity started to be detected at 2 min after the start of the experiment. Thus, it was shown that low molecular weight heparin was released from the percutaneously absorbable preparation made in this example with a sustained-release manner.

TABLE 7

| Elapsed time after the start of dissolution experiment (min) | | 0 | 1 | 2 | 3 | 4 | 5 | 10 | 30 | 60 | 120 | 180 |
|---|---|---|---|---|---|---|---|---|---|---|---|---|
| Anti-Xa activity (IU/mL) | Example 17 | ND | ND | 0.10 | 0.16 | 0.18 | 0.19 | 0.19 | 0.19 | 0.19 | 0.19 | 0.19 |
| | Example 18 | ND | ND | ND | ND | ND | ND | ND | 0.09 | 0.12 | 0.18 | 0.19 |

Example 19

This example illustrates a percutaneously absorbable preparation having a needle-like and filamentous shape and containing insulin (active substance) held in a base consisting of human serum albumin, where the insulin was released with a sustained-released manner.

About 0.2 mL of distilled water was added to 150 mg of human serum albumin to be dissolved. The solution was mixed well to give a base paste consisting of human serum albumin. To 100 mg of this base, 10 μL of sodium insulin solution (100 mg/mL, private processed product) was added well mixed so that insulin was held in the base paste. To this base paste holding insulin, a top of a polypropylene stick of which diameter was about 2 mm was attached. Thereafter, the top was gradually pulled apart so that the base paste attaching to the top has a needle-like or filamentous shape. Thereafter, glutaraldehyde treatment was performed in the same way as Example 18 to give a percutaneously absorbable preparation having a needle-like or filamentous shape.

Example 20

This example illustrates a percutaneously absorbable preparation having a needle-like and filamentous shape and containing insulin (active substance) held in porous anhydrous silicate or porous calcium silicate (porous material), where the insulin was released with a sustained-released manner.

Four kinds of porous anhydrous silicates (Trade names: Sylysia350, Sylysia440, Sylysia550 and Sylysia730 (Fuji Silysia Co., Ltd. Aichi, Japan)), and one kind of porous calcium silicate (Trade name: Florite RE, Eisai) were examined as porous materials. In the following, example using Sylysia 350 is named Example 20-1, example using Sylysia 440 is named Example 20-2, example using Sylysia 550 is named Example 20-3, example using Sylysia 730 is named Example 20-4 and example using Florite is named Example 20-5. On the other hand, bovine pancreatic insulin (Wako Pure Chemical Industries) was dissolved with distilled water to give 9.6 mg/mL insulin solution. To 15.9 mg of porous material, 0.1 mL of the insulin solution was added. The solution was mixed well and dried to give insulin-adsorbed powder. On the other hand, about 0.15 mL of distilled water was added to 317.5 mg of sodium chondroitin sulfate C (Nacalai Tesque) to be dissolved. The solution was mixed well to give a base paste consisting of sodium chondroitin sulfate C. To this base paste, 16.86 mg of insulin-adsorbed powder was added and mixed well. To this base paste containing porous material in which insulin was held, a top of a glass stick of which diameter was about 3 mm was attached. Thereafter, the top was gradually pulled apart so that the base paste attaching to the top has a needle-like or filamentous shape. The needle-like or filamentous base paste was solidified by drying at low temperature to give a percutaneously absorbable preparation having a needle-like or filamentous shape, resulting in giving five kinds of percutaneously absorbable preparations. Evaluation in animal experiment using mice was performed at the same time with Example 21 after-described.

Example 21

This example illustrates a percutaneously absorbable preparation having a needle-like and filamentous shape, containing middle-acting insulin (active substance) held in a base, and further containing L-glutamic acid-L-lysine (thread-reducing reagent), where the insulin was released with a sustained-released manner.

About 0.45 mL of distilled water was added to 312.8 mg of sodium chondroitin sulfate C (Nacalai Tesque) and 153.8 mg of L-glutamic acid-L-lysine (Ajinomoto) to be dissolved. The solution was mixed well to give a base paste consisting of sodium chondroitin sulfate C. To this base paste, 0.167 IU of middle-acting insulin (Penfil N™, NovoNordisc) was added and well mixed so that middle-acting insulin was held in the base paste. To this base paste holding middle-acting insulin, a top of a glass stick of which diameter was about 3 mm was attached. Thereafter, the top was gradually pulled apart so that the base paste attaching to the top has a needle-like or filamentous shape. The needle-like or filamentous base paste was solidified by drying at low temperature to give a percutaneously absorbable preparation having a needle-like or filamentous shape.

Figure 16A:
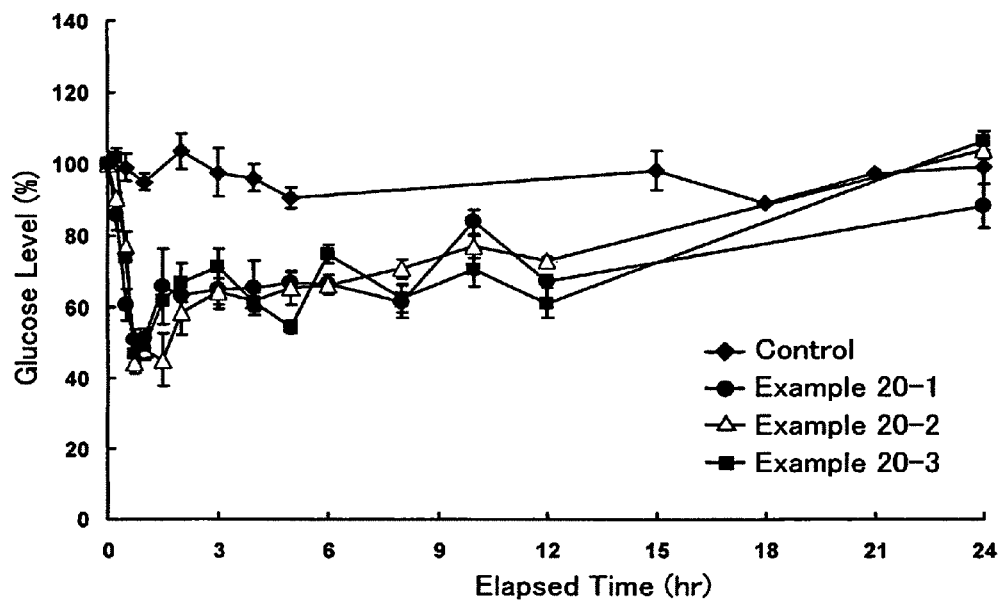
FIG. 16A is a graph depicting the blood glucose level vs. time profiles after the administration of the percutaneously absorbable preparations in Example 20-1, 20-2 or 20-3.
Figure 16B:
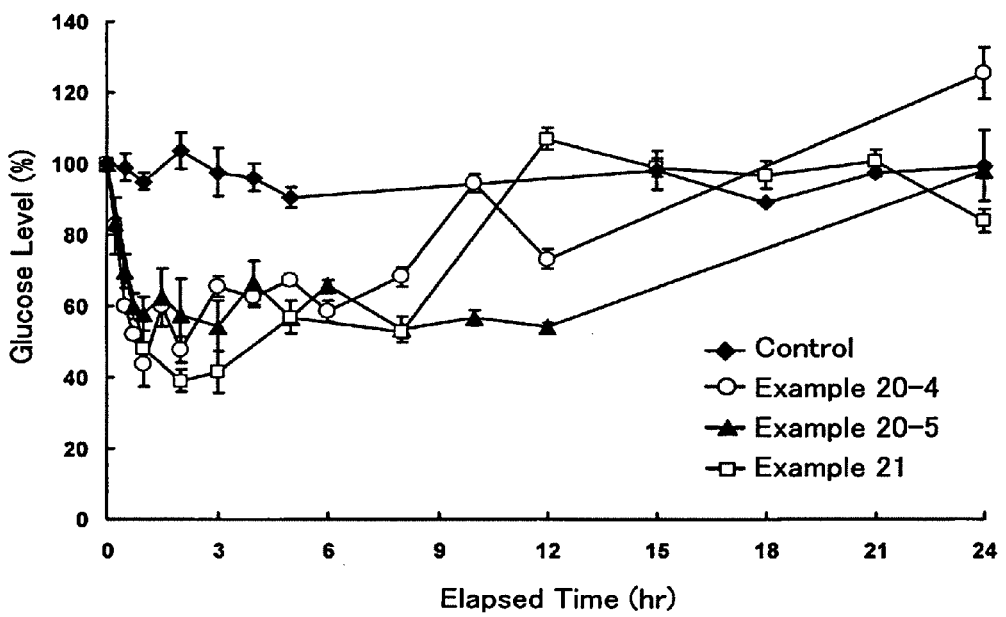
FIG. 16B is a graph depicting the blood glucose level vs. time profiles after the administration of the percutaneously absorbable preparations in Example 20-4, 20-5 or 21.

The percutaneously absorbable preparations made in Examples 20 and 21 were evaluated by means of hypoglycemic effect in mice. More specifically, mice, about 30 g body weight, were anesthetized by an injection of pentobarbital and were fixed on the operating-table after the hair of the abdomen was shaved. Percutaneously absorbable preparations made in Example 20 or 21 were inserted into the mice abdominal skin and insulin was administered percutaneously. The dose was 2.5 IU/kg. Systemic blood was removed before and after administration for 24 hr. Serum samples were prepared from the obtained blood samples and glucose concentration in each serum sample was measured using glucose assay kit (Glucose C II-Test kit, Wako Pure Chemical Industries). Each glucose level was shown as a relative value to the pre-dose level, 100%. All data were calculated as the mean+/−standard deviation (SD), wherein each group consists of three to four mice. The result is shown in FIGS. 16A and 16B. These figures show the time course of blood glucose levels when percutaneously absorbable preparations of Example 20 or 21 were inserted into the skin. FIG. 16A shows the time course of blood glucose levels when percutaneously absorbable preparations of Example 20-1, 20-2 or 20-3 were inserted into the skin. FIG. 16B shows the time course of blood glucose levels when percutaneously absorbable preparations of Example 20-4, 20-5 or 21 were inserted into the skin. The ordinate of FIGS. 16A and 16B is blood glucose level and abscissa is the time. Control is the case where percutaneously absorbable preparations consisting of only base were used. As a result, in five kinds of the percutaneously absorbable preparations of Example 20, serum glucose levels decreased for 12 hr after administration. Furthermore, in the percutaneously absorbable preparations of Example 21, serum glucose levels decreased for 9 hr after administration. From these results, it was shown that insulin was administered percutaneously with a sustained-release manner by the percutaneously absorbable preparations of Example 20 or 21.

Example 22

This example illustrates a percutaneously absorbable preparation having a needle-like and filamentous shape and containing insulin (active substance) held in a base consisting of hyaluronic acid and dextran.

Thirty holes of about 1 mm in the diameter were made on an acrylic plate of about 2.0 mm in thickness. Sawing needles were penetrated to these holes and were fixed where the needle top comes out of the surface of an acrylic plate about 200 μm. In addition, adhesive glue was injected from the inserted side of the needles and the needles were fixed to an acrylic plate. On the other hand, silicon resin was put in a petri dish. An acrylic plate with the above-mentioned needles was put on the silicon resin in the petri dish, and was left overnight. An acrylic plate with needles was removed after the silicon resin was confirmed to be solid, and the mold made of the silicon resin was made.

To 2.4 mg of hyaluronic acid (mean molecular weight: 90,000, commodity code: FCH-SU by Kibun Food Chemifa Co., Ltd.) and 2.4 mg of dextran (molecular weight: 50,000-70,000, Nacarai Tesque) to be dissolved, 2.5 μL of distilled water was added. The solution was mixed well to give a base paste consisting of hyaluronic acid and dextran. To this base paste, 0.2 mg of sodium insulin (private processed product) solution was added and well mixed so that insulin was held in the base paste. The base paste holding insulin was filled into the mold made of silicon. The filled base paste was solidified by drying at low temperature. The solidified base was removed from the mold to give a percutaneously absorbable preparation having a needle-like or filamentous shape.

Example 23

This example illustrates a percutaneously absorbable preparation having a needle-like and filamentous shape and containing vitamin C (active substance) held in a base consisting of chitosan.

One hundred μL of acetic acid and about 1 mL of distilled water were added to 0.3 g of chitosan (Daikitosan VL, Dainichiseika Color & Chemicals Mfg. Co., Ltd.) to be dissolved. The solution was mixed well under stirring on a hot plate stirrer. Further, 1N NaOH solution was added so that pH of the solution was adjusted to about 6.5. This solution was stirred under warm air blow and water was evaporated to give a base paste consisting of chitosan. To this base paste, 5 mg of vitamin C (L-ascorbic acid, Wako Pure Chemical Industries) was added and well mixed so that vitamin C was held in the base paste. The base paste holding vitamin C was filled into the mold in the same way as Example 22. The filled base paste was solidified by drying at low temperature to give a percutaneously absorbable preparation having a needle-like or filamentous shape.

Example 24

This example illustrates a percutaneously absorbable preparation having a needle-like and filamentous shape and containing insulin (active substance) held in a base consisting of sodium chondroitin sulfate C, where the insulin was released with a sustained-released manner.

To 4.8 mg of sodium chondroitin sulfate C (Nacalai Tesque) to be dissolved, 2.5 μL it of distilled water was added. The solution was mixed well to give a base paste consisting of sodium chondroitin sulfate C. To this base paste, 0.2 mg of sodium insulin (private processed product) was added and well mixed so that insulin was held in the base paste. To this base holding sodium chondroitin sulfate C, a top of a polypropylene tip was attached. Thereafter, the top was gradually pulled apart so that the base paste attaching to the top has a needle-like or filamentous shape. The needle-like or filamentous base paste was soaked in a saturated calcium chloride solution for 1 hr at 4° C. and was hardened. Through this process, water-insoluble layer was made on its surface. The layer was dried in air to give a percutaneously absorbable preparation having a needle-like or filamentous shape.

The invention claimed is:

1. A percutaneously absorbable preparation adapted for insertion into skin to percutaneously administer an objective substance into the body, comprising a base consisting of a water-soluble polymer substance and the objective substance held in the base,
   wherein the polymer substance is at least one substance selected from the group consisting of sodium chondroitin sulfate, hyaluronic acid, glycogen, pullulan, serum alpha-acid glycoprotein and carboxyvinyl polymer, optionally in combination with dextran,
   wherein the percutaneously absorbable preparation has two opposed ends, wherein one opposed end is a pointed tip and the other opposed end is a pushing part, provided that when the pointed tip end of the percutaneously absorbable preparation is placed on the skin, the percutaneously absorbable preparation has sufficient physical strength to be inserted into the skin by pushing on the pushing part end, and
   wherein the percutaneously absorbable preparation has substantially conical shape having a diameter and a length, wherein the diameter of the pushing part is in a range of 0.1-500 micrometer, and the length is in a range of 0.5-1500 micrometer.

2. The percutaneously absorbable preparation of claim 1 which is produced without being exposed to a temperature of more than 50° C.

3. A patch comprising
   a carrier sheet having an exterior surface, and
   the percutaneously absorbable preparation of claim 1 attached to the external surface,
   wherein the patch is configured so that the pointed tip of the percutaneously absorbable preparation is capable of being inserted into the skin by pushing on the carrier sheet.

* * * * *